(12) United States Patent
Fukumoto et al.

(10) Patent No.: US 8,859,183 B2
(45) Date of Patent: Oct. 14, 2014

(54) N-ACYL-β-LACTAM DERIVATIVE, MACROMOLECULAR COMPOUND, AND PHOTORESIST COMPOSITION

(71) Applicants: Takashi Fukumoto, Tainai (JP); Shuji Matsunaga, Saijo (JP); Miki Tsuruta, Kurashiki (JP)

(72) Inventors: Takashi Fukumoto, Tainai (JP); Shuji Matsunaga, Saijo (JP); Miki Tsuruta, Kurashiki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 13/958,063

(22) Filed: Aug. 2, 2013

(65) Prior Publication Data

US 2014/0038106 A1    Feb. 6, 2014

Related U.S. Application Data

(63) Continuation of application No. 13/392,129, filed as application No. PCT/JP2010/064604 on Aug. 27, 2010, now Pat. No. 8,753,794.

(30) Foreign Application Priority Data

Aug. 28, 2009   (JP) ................. 2009-199026

(51) Int. Cl.

| | | |
|---|---|---|
| *C07D 205/08* | (2006.01) | |
| *G03F 7/004* | (2006.01) | |
| *C08F 26/06* | (2006.01) | |
| *G03F 7/039* | (2006.01) | |
| *C08F 226/06* | (2006.01) | |
| *C08F 20/26* | (2006.01) | |
| *C08F 20/34* | (2006.01) | |

(52) U.S. Cl.
CPC ............ *G03F 7/0397* (2013.01); *C08F 226/06* (2013.01); *C07D 205/08* (2013.01); *C08F 20/26* (2013.01); *C08F 20/34* (2013.01); *G03F 7/039* (2013.01)
USPC .................... 430/270.1; 526/258; 540/200

(58) Field of Classification Search
CPC ..... G03F 7/004; G03F 7/033; C07D 2005/00; C07D 205/04; C07D 205/06; C07D 205/08; C07D 205/12; C07D 205/00; C08F 226/00; C08F 226/06

USPC ........ 430/270.1; 526/258, 259, 264; 540/200, 540/203
See application file for complete search history.

(56) References Cited

U.S. PATENT DOCUMENTS

| | | | | |
|---|---|---|---|---|
| 3,626,030 | A * | 12/1971 | Wolters et al. ................ 524/343 |
| 5,594,134 | A | 1/1997 | Ho et al. | |
| 6,200,725 | B1 | 3/2001 | Takechi et al. | |
| 8,592,129 | B2 * | 11/2013 | Ichikawa et al. ........... 430/270.1 |
| 2008/0026331 | A1 | 1/2008 | Hasegawa et al. | |
| 2011/0053082 | A1 * | 3/2011 | Ichikawa et al. ........... 430/270.1 |
| 2011/0196122 | A1 | 8/2011 | Maeda et al. | |
| 2012/0070778 | A1 * | 3/2012 | Ichikawa et al. ........... 430/270.1 |
| 2012/0183900 | A1 * | 7/2012 | Tsuchiya et al. ........... 430/270.1 |

FOREIGN PATENT DOCUMENTS

| | | |
|---|---|---|
| DE | 1 218 718 | 6/1966 |
| DE | 1 258 604 | 1/1968 |
| JP | 1 501470 | 5/1989 |
| JP | 2001-188346 | 7/2001 |

OTHER PUBLICATIONS

International Search Report Issued Nov. 30, 2010 in PCT/JP10/64604 Filed Aug. 27, 2010.

* cited by examiner

*Primary Examiner* — Anca Eoff
(74) *Attorney, Agent, or Firm* — Oblon, Spivak, McClelland, Maier & Neustadt, L.L.P.

(57) ABSTRACT

Provided are N-acyl-β-lactam derivatives represented by the following general formula, from which a photoresist composition capable of controlling an acid diffusion length to be short is obtained; a polymer obtained by polymerizing the N-acyl-β-lactam derivative represented by the following general formula as one of starting materials; and a photoresist composition containing the polymer,

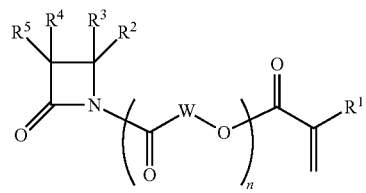

where the structural variables are as defined herein.

10 Claims, 3 Drawing Sheets

N-ACYL-β-LACTAM DERIVATIVE, MACROMOLECULAR COMPOUND, AND PHOTORESIST COMPOSITION

This application is a Continuation of U.S. application Ser. No. 13/392,129, filed on Feb. 24, 2012, which is a National Stage of PCT/JP10/64604, filed Aug. 27, 2010.

TECHNICAL FIELD

The present invention relates to an N-acyl-β-lactam derivative, a polymer obtained by polymerizing at least the N-acyl-β-lactam derivative as one of starting materials, and a photoresist composition having a short acid diffusion length, in which a line width roughness (LWR) is improved and from which a resist pattern having a high resolution is formed.

BACKGROUND ART

In recent years, in the field of manufacture of electronic devices represented by the manufacture of integrated circuit devices, requirements for high integration of devices are increasing, and it is known that the structure of a polymer in a photoresist composition influences the formation of a fine pattern.

In the photoresist composition, lithography properties such as sensitivity to an exposure light source, resolution capable of forming a pattern having fine dimensions, and the like are required, and therefore, Chemically amplified photoresist compositions composed of an acid dissociable functional group-containing polymer and a compound capable of generating an acid upon irradiation with radiations (hereinafter referred to as "exposure") (the latter compound will be hereinafter referred to as "photo acid generator") is used. The acid dissociable functional group-containing polymer is based on a structure in which a part of an alkali easily soluble site of an alkali soluble polymer is protected by an appropriate acid dissociable functional group, and the selection of such an acid dissociable functional group is very important in view of regulating a function as a photoresist composition.

As the already-known acid dissociable functional group-containing polymer which is incorporated into the photoresist composition, for example, there are known polymers obtained by polymerizing a material containing an adamantyl group-containing acrylic ester (see Patent Document 1); polymers having, as a constituent unit, a lactone skeleton-containing acrylic ester introduced thereinto (see Patent Document 2); polymers having a norbornane lactone skeleton-containing constituent unit (see Patent Documents 3 to 5); and the like.

PRIOR ART DOCUMENTS

Patent Documents

Patent Document 1: JP-A-9-73173
Patent Document 2: JP-A-9-90637
Patent Document 3: JP-A-2000-26446
Patent Document 4: JP-A-2001-188346
Patent Document 5: JP-A-2008-31298

SUMMARY OF THE INVENTION

Problems to be Solved by the Invention

One of important problems of the lithography technology of recent years is to minimize a line width fluctuation of a formed pattern, which is called a line width roughness (LWR). However, in photoresist compositions containing each of the polymers disclosed in Patent Documents 1 to 5, the LWR cannot be sufficiently reduced, and therefore, there is room for more improvement.

Then, an object of the present invention is to provide a novel compound capable of obtaining a photoresist composition from which a high-resolution resist pattern having improved LWR is formed, a polymer obtained by polymerizing at least the novel compound as one of starting materials, and a photoresist composition containing the polymer.

Means for Solving the Problems

In order to solve the foregoing problems, the present inventors made extensive and intensive investigations. As a result, it has been found that by using a photoresist composition using a compound capable of controlling an acid diffusion length to be short, the LWR can be improved and that a resist pattern having a high resolution is formed.

That is, the present invention provides the following [1] to [6].

[1] An N-acyl-β-lactam derivative represented by the following general formula (1):

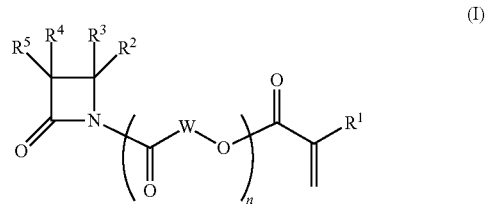

(in the formula, $R^1$ represents a hydrogen atom, a methyl group, or a trifluoromethyl group; W represents an alkylene group having a carbon number of from 1 to 10 or a cycloalkylene group having a carbon number of from 4 to 10; n represents 0 or 1; and each of $R^2$, $R^3$, $R^4$, and $R^5$ independently represents a hydrogen atom, an alkyl group having a carbon number of from 1 to 5, a cyclic hydrocarbon group having a carbon number of from 3 to 10, or an acyloxy group having a carbon number of from 2 to 6, provided that 1) $R^2$ and $R^3$, or $R^4$ and $R^5$, may be connected to each other to form a substituted or unsubstituted ring having a ring forming atom number of from 3 to 10, which may have an oxygen atom at an arbitrary position, 2) $R^3$ and $R^4$ may be connected to each other to form a substituted or unsubstituted ring having a ring forming atom number of from 4 to 10, which may have an oxygen atom at an arbitrary position, and 3) all of $R^2$, $R^3$, $R^4$, and $R^5$ are not a hydrogen atom at the same time.)

[2] The N-acyl-β-lactam derivative as set forth above in [1], which is represented by the following general formula (1-1):

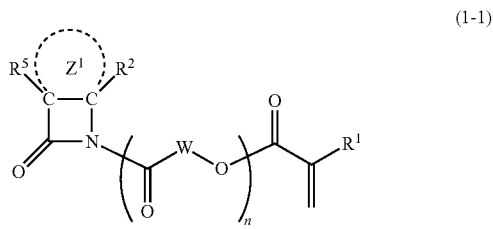

(in the formula (1-1), $R^1$ represents a hydrogen atom, a methyl group, or a trifluoromethyl group; each of $R^2$ and $R^5$ independently represents a hydrogen atom or an alkyl group having a carbon number of from 1 to 5; W represents an alkylene group having a carbon number of from 1 to 10 or a cycloalkylene group having a carbon number of from 4 to 10; n represents 0 or 1; and $Z^1$ represents a ring formed together with the two carbon atoms on the β-lactam, with a number of atoms forming the ring being from 3 to 10.)

[3] The N-acyl-β-lactam derivative as set forth above in [1], which is represented by the following general formula (1-2):

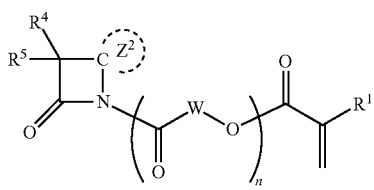

(1-2)

(in the formula (1-2), $R^1$ represents a hydrogen atom, a methyl group, or a trifluoromethyl group; each of $R^4$ and $R^5$ independently represents a hydrogen atom or an alkyl group having a carbon number of from 1 to 5; W represents an alkylene group having a carbon number of from 1 to 10 or a cycloalkylene group having a carbon number of from 4 to 10; n represents 0 or 1; and $Z^2$ represents an aliphatic ring formed together with the carbon atom on the β-lactam, with a carbon number forming the aliphatic ring being from 3 to 10.)

[4] The N-acyl-β-lactam derivative as set forth above in [1], which is represented by the following general formula (1-3):

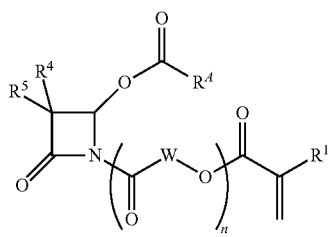

(1-3)

(in the formula (1-3), $R^A$ represents a hydrogen atom, a methyl group, or a trifluoromethyl group; each of $R^4$ and $R^5$ independently represents a hydrogen atom or an alkyl group having a carbon number of from 1 to 5; W represents an alkylene group having a carbon number of from 1 to 10 or a cycloalkylene group having a carbon number of from 4 to 10; n represents 0 or 1; and $R^A$ represents an alkyl group having a carbon number of from 1 to 5 or a cyclic hydrocarbon group having a carbon number of from 3 to 10.)

[5] A polymer obtained by polymerizing the N-acyl-β-lactam derivative as set forth above in any one of [1] to [4].

[6] A photoresist composition containing the polymer as set forth above in [5], a photo acid generator, and a solvent.

Effects of the Invention

According to the photoresist composition of the present invention, by controlling the acid diffusion length to be short, the LWR can be improved, and a resist pattern having a high resolution is formed.

MODES FOR CARRYING OUT THE INVENTION

[N-Acyl-β-lactam Derivative]

Figure 1:
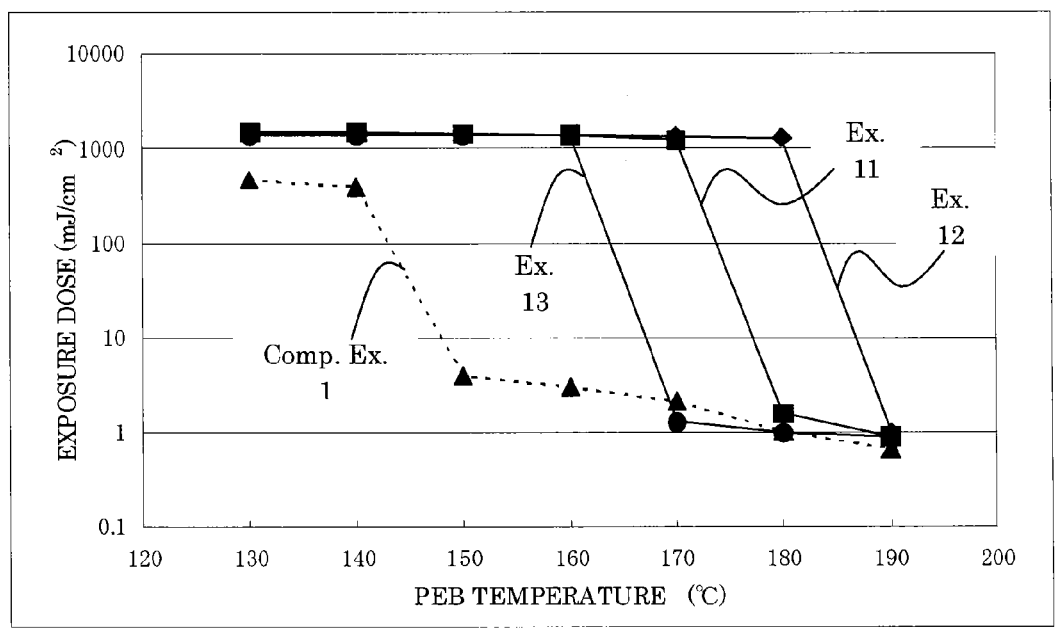
FIG. 1 is a graph showing a correlation between a post-exposure bake (PEB) temperature of each of photoresist films formed from Photoresist Compositions A to C obtained in Examples 11 to 13 and Photoresist Composition F obtained in Comparative Example 1 and an exposure dose of light irradiated until the photoresist film has caused film dissolution.

In order to obtain a photoresist composition which controls an acid diffusion length to be short, an N-acyl-β-lactam derivative represented by the following general formula (1) (hereinafter referred to as "N-acyl-β-lactam derivative (1)") is useful.

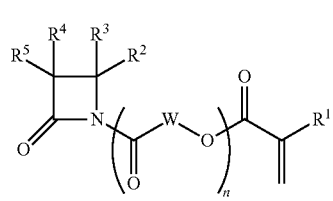

(1)

In the foregoing general formula (1), $R^1$ represents a hydrogen atom, a methyl group, or a trifluoromethyl group.

W represents an alkylene group having a carbon number of from 1 to 10 or a cycloalkylene group having a carbon number of from 4 to 10.

Examples of the alkylene group having a carbon number of from 1 to 10, which W represents, include a methylene group, an ethane-1,1-diyl group, an ethane-1,2-diyl group, a propane-1,1-diyl group, a propane-1,2-diyl group, a propane-1,3-diyl group, a pentane-1,5-diyl group, a hexane-1,1-diyl group, and so on. Of these, from the viewpoint of obtaining a photoresist composition whose acid diffusion length is controlled to be short, a methylene group and an ethane-1,1-diyl group are preferable. Also, examples of the cycloalkylene group having a carbon number of from 4 to 10, which W represents, include a cyclohexane-1,2-diyl group, a cyclohexane-1,4-diyl group, a cyclodecane-1,5-diyl group, and so on.

n represents 0 or 1, and from the viewpoint of obtaining a photoresist composition whose acid diffusion length is controlled to be short, n is preferably 0.

In the foregoing general formula (1), each of $R^2$, $R^3$, $R^4$, and $R^5$ independently represents a hydrogen atom, an alkyl group having a carbon number of from 1 to 5, a cyclic hydrocarbon group having a carbon number of from 3 to 10, or an acyloxy group, provided that 1) $R^2$ and $R^3$, or $R^4$ and $R^5$, may be connected to each other to form a substituted or unsubstituted ring having a ring forming atom number of from 3 to 10, which may have an oxygen atom at an arbitrary position, 2) $R^3$ and $R^4$ may be connected to each other to form a substituted or unsubstituted ring having a ring forming atom number of from 4 to 10, which may have an oxygen atom at an arbitrary position, and 3) all of $R^2$, $R^3$, $R^4$, and $R^5$ are not a hydrogen atom at the same time.

Examples of the alkyl group having a carbon number of from 1 to 5, which each of $R^2$, $R^3$, $R^4$, and $R^5$ independently represents, include a methyl group, an ethyl group, an n-propyl group, an isopropyl group, an n-butyl group, an isobutyl group, a t-butyl group, an n-pentyl group, an isopentyl group, an s-pentyl group, a t-pentyl group, and so on.

Examples of the cyclic hydrocarbon group having a carbon number of from 3 to 10, which each of $R^2$, $R^3$, $R^4$, and $R^5$ independently represents, include a cyclopropyl group, a cyclobutyl group, a cyclopentyl group, a cyclohexyl group, a 1-adamantyl group, a bicyclo[2.2.1]heptan-1-yl group, and so on.

Examples of the acyloxy group which each of $R^2$, $R^3$, $R^4$, and $R^5$ independently represents include an acetyloxy group, a propionyloxy group, a butyryloxy group, and so on.

Also, examples of the ring having a ring forming atom number of from 3 to 10, which $R^2$ and $R^3$, or $R^4$ and $R^5$, may be connected to each other to form and which may have an oxygen atom at an arbitrary position, include a cyclopropane ring, a cyclobutane ring, a cyclopentane ring, a cyclohexane ring, a cycloheptane ring, a camphane ring, a norbornane ring, an adamantane ring, a tetrahydrofuran ring, a tetrahydropyran ring, and so on. The ring may have a substituent, and examples of the substituent include an acetyloxy group, a propionyloxy group, a cyano group, a nitro group, and so on.

Examples of the ring having a ring forming atom number of from 4 to 10, which $R^3$ and $R^4$ may be connected to each other to form and which may have an oxygen atom at an arbitrary position, include a cyclobutane ring, a cyclopentane ring, a cyclohexane ring, a cycloheptane ring, a cyclooctane ring, a bicyclo[2.2.1]heptane ring, a tricyclo[5.2.1.0$^{2.6}$]decane ring, a tetrahydrofuran ring, a tetrahydropyran ring, and so on. The ring may have a substituent, and examples of the substituent include an acetyloxy group, a propionyloxy group, a cyano group, a nitro group, and so on.

Among those of the foregoing general formula (1), from the viewpoint of obtaining a photoresist composition whose acid diffusion length is controlled to be short, N-acyl-β-lactam derivatives represented by the following general formulae (1-1) to (1-3) are preferable.

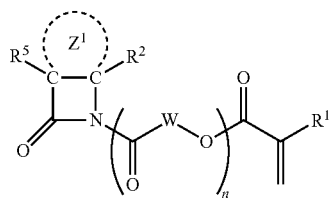

(1-1)

In the foregoing general formula (1-1), $R^1$ represents a hydrogen atom, a methyl group, or a trifluoromethyl group. Each of $R^2$ and $R^5$ independently represents a hydrogen atom or an alkyl group having a carbon number of from 1 to 5. W represents an alkylene group having a carbon number of from 1 to 10 or a cycloalkylene group having a carbon number of from 4 to 10. n represents 0 or 1. Specific examples of these groups are the same groups as those described regarding $R^1$, $R^2$, $R^5$, W, and n in the general formula (1), and preferred examples thereof are also the same.

Also, $Z^1$ represents a ring formed together with the two carbon atoms on the β-lactam, with a number of atoms forming the ring being from 3 to 10. Examples of the ring include an aliphatic ring and an ether ring in which an arbitrary carbon atom of the aliphatic ring is converted into an oxygen atom. Examples of the aliphatic ring include a cyclopropane ring, a cyclobutane ring, a cyclopentane ring, a cyclohexane ring, a cycloheptane ring, a cyclooctane ring, a bicyclo[2.2.1]heptane ring, a tricyclo[5.2.1.0$^{2.6}$]decane ring, and so on. Also, examples of the ether ring include a tetrahydrofuran ring, a tetrahydropyran ring, and so on. The ring structure may have a substituent, and examples of the substituent include an alkyl group having a carbon number of from 1 to 10 (preferably from 1 to 5), such as a methyl group, an ethyl group, and the like; an acyloxy group having a carbon number of from 2 to 10 (preferably from 2 to 6), such as an acetyloxy group, a propionyloxy group, and the like; a cyano group; a nitro group; and so on.

From the viewpoint of obtaining a photoresist composition whose acid diffusion length is controlled to be short, $Z^1$ is preferably a cyclopentane ring or a tricyclo[5.2.1.0$^{2.6}$]decane ring.

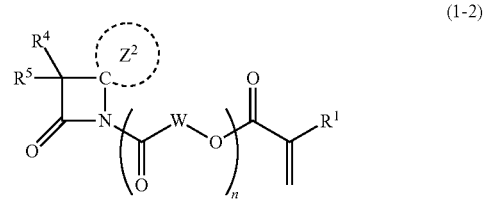

(1-2)

In the foregoing general formula (1-2), $R^1$ represents a hydrogen atom, a methyl group, or a trifluoromethyl group. Each of $R^4$ and $R^5$ independently represents a hydrogen atom or an alkyl group having a carbon number of from 1 to 5. W represents an alkylene group having a carbon number of from 1 to 10 or a cycloalkylene group having a carbon number of from 4 to 10. n represents 0 or 1. Specific examples of these groups are the same groups as those described regarding $R^1$, $R^4$, $R^5$, W, and n in the general formula (1), and preferred examples thereof are also the same.

Also, $Z^2$ represents an aliphatic ring formed together with the carbon atom on the β-lactam, with a carbon number forming the aliphatic ring being from 3 to 10. Examples of the aliphatic ring include a cyclopropane ring, a cyclobutane ring, a cyclopentane ring, a cyclohexane ring, a cycloheptane ring, a cyclooctane ring, a bicyclo[2.2.1]heptane ring, a tricyclo [5.2.1.0$^{2.6}$]decane ring, an adamantane ring, and so on. The ring structure may have a substituent, and examples of the substituent include an alkyl group having a carbon number of from 1 to 10 (preferably from 1 to 5), such as a methyl group, an ethyl group, and the like; an acyloxy group having a carbon number of from 2 to 10 (preferably from 2 to 6), such as an acetyloxy group, a propionyloxy group, and the like; a cyano group; a nitro group; and so on.

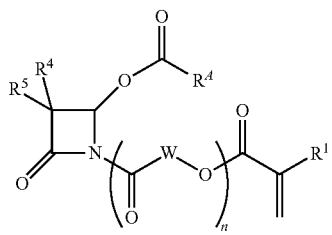

(1-3)

In the foregoing general formula (1-3), $R^1$ represents a hydrogen atom, a methyl group, or a trifluoromethyl group. Each of $R^4$ and $R^5$ independently represents a hydrogen atom or an alkyl group having a carbon number of from 1 to 5. W represents an alkylene group having a carbon number of from 1 to 10 or a cycloalkylene group having a carbon number of from 4 to 10. n represents 0 or 1. Specific examples of these groups are the same groups as those described regarding $R^1$, $R^4$, $R^5$, W, and n in the general formula (1), and preferred examples thereof are also the same.

Also, $R^4$ represents an alkyl group having a carbon number of from 1 to 5 or a cyclic hydrocarbon group having a carbon number of from 3 to 10. Examples of the alkyl group having a carbon number of from 1 to 5 include a methyl group, an ethyl group, an n-propyl group, an isopropyl group, an n-butyl group, an isobutyl group, a t-butyl group, an n-pentyl group, an isopentyl group, an s-pentyl group, a t-pentyl group, and so on. Examples of the cyclic hydrocarbon group having a carbon number of from 3 to 10 include a cyclic aliphatic hydrocarbon group such as a cyclopropyl group, a cyclobutyl group, a cyclopentyl group, a cyclohexyl group, an adamantyl group, a bicyclo[2.2.1]heptan-1-yl group, a tricyclo[5.2.1.0$^{2.6}$]decan-8-yl group, and the like, and a cyclic hydrocarbon group having a carbon number of from 4 to 6 is preferable. Incidentally, from the viewpoint of obtaining a photoresist composition whose acid diffusion length is controlled to be short, $R^4$ is preferably a methyl group.

(Manufacturing Method of N-acyl-β-lactam Derivative (1))

Though a manufacturing method of the N-acyl-β-lactam derivative (1) is not particularly limited, for example, the N-acyl-β-lactam derivative (1) can be manufactured by the following step.

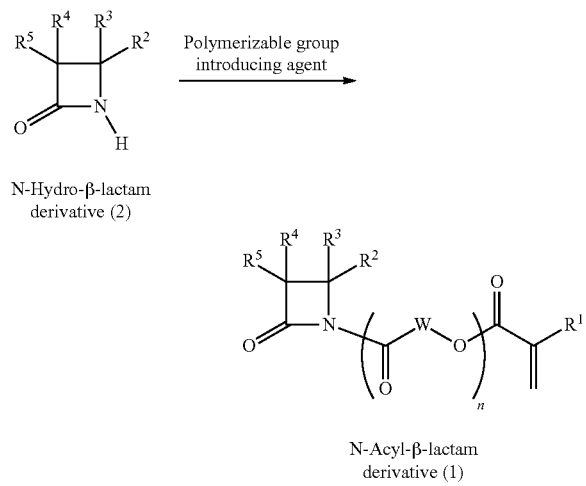

The N-acyl-β-lactam derivative (1) wherein n is 0 can be manufactured by the following polymerizable group introducing step-A.

In the polymerizable group introducing step-A, the foregoing N-hydro-β-lactam derivative (2) is allowed to react with a compound represented by a formula: $CH_2=CR^1COX^1$ (in the formula, $R^1$ is the same as defined above; and $X^1$ represents a chlorine atom, a bromine atom, or an iodine atom), a formula: $(CH_2=CR^1CO)_2O$ (in the formula, $R^1$ is the same as defined above) a formula: $CH_2=CR^1COOC(=O)R^6$ (in the formula, $R^1$ is the same as defined above; and $R^6$ represents a t-butyl group or a 2,4,6-trichlorophenyl group), or a formula: $CH_2=CR^1COOSO_2R^7$ (in the formula, $R^1$ is the same as defined above; and $R^7$ represents a methyl group or a p-tolyl group) (such a compound will be hereinafter referred to as "polymerizable group introducing agent A") in the presence of a basic substance.

The N-acyl-β-lactam derivative (1) wherein n is 1 can be manufactured by the following polymerizable group introducing step-B. Incidentally, the polymerizable group introducing step-B is composed of polymerizable group introducing steps-B1 and B2.

In the polymerizable group introducing step-B1, the foregoing N-hydro-β-lactam derivative (2) is allowed to react with a compound represented by a formula: $X^2—W—COX^3$ (in the formula, W is the same as defined above; and each of $X^2$ and $X^3$ independently represents a chlorine atom, a bromine atom, or an iodine atom), a formula: $(X^2—W—CO)_2O$ (in the formula, $X^2$ and W are the same as defined above), a formula: $X^2—W—COOC(=O)R^8$ (in the formula, $X^2$ and W are the same as defined above; and $R^8$ represents a t-butyl group or a 2,4,6-trichlorophenyl group), or a formula: $X^2—W—COOSO_2R^9$ (in the formula, $X^2$ and W are the same as defined above; and $R^9$ represents a methyl group or a p-tolyl group) (such a compound will be hereinafter referred to as "connecting group introducing agent B1") in the presence of a basic substance.

Subsequently, as the polymerizable group introducing step-B2, the resultant is allowed to react with a compound represented by a formula: $CH_2=CR^1COOM$ (in the formula, $R^1$ is the same as defined above; and M represents a sodium atom or a potassium atom) (this compound will be hereinafter referred to as "polymerizable group introducing agent B2").

The polymerizable group introducing step-A and the polymerizable group introducing step-B are hereunder described in succession.

(Polymerizable Group Introducing Step-A)

Among the polymerizable group introducing agents A which are used in the polymerizable group introducing step-A, examples of the compound represented by the formula: $CH_2=CR^1COX^1$ include acryloyl chloride, methacryloyl chloride, and the like. Examples of the compound represented by the formula: $(CH_2=CR^1CO)_2O$ include acrylic anhydride, methacrylic anhydride, and the like. Examples of the compound represented by the formula: $CH_2=CR^1COOC(=O)R^6$ include acrylic pivalic anhydride, acrylic 2,4,6-trichlorobenzoic anhydride, methacrylic pivalic anhydride, methacrylic 2,4,6-trichlorobenzoic anhydride, and the like. Examples of the compound represented by the formula: $CH_2=CR^1COOSO_2R^7$ include acrylic methanesulfonic anhydride, acrylic p-toluenesulfonic anhydride, methacrylic methanesulfonic anhydride, methacrylic p-toluenesulfonic anhydride, and the like.

Though a use amount of the polymerizable group introducing agent A is not particularly limited, from the viewpoints of economy and easiness in post-treatment, it is preferably from 0.8 to 5 mol, and more preferably from 0.8 to 3 mol per 1 mol of the N-hydro-β-lactam derivative (2).

Examples of the basic substance which is used in the polymerizable group introducing step-A include an alkali metal hydride such as sodium hydride, potassium hydride, and the like; an alkali metal hydroxide such as sodium hydroxide, potassium hydroxide, and the like; an alkali metal carbonate such as sodium carbonate, potassium carbonate, and the like; a tertiary amine such as triethylamine, tributylamine, diazabicyclo[2.2.2]octane, and the like; a nitrogen-containing heterocyclic aromatic compound such as pyridine and the like; and so on. Of these, a tertiary amine and a nitrogen-containing heterocyclic aromatic compound are preferable.

Though a use amount of the basic substance is not particularly limited, from the viewpoints of economy and easiness in post-treatment, it is preferably from 0.8 to 5 mol, and more preferably from 0.8 to 3 mol per 1 mol of the N-hydro-β-lactam derivative (2).

The polymerizable group introducing step-A is carried out in the presence or absence of a solvent.

The solvent is not particularly limited so far as it does not inhibit the reaction. For example, there are preferably exemplified an aliphatic hydrocarbon such as hexane, heptane, octane, and the like; an aromatic hydrocarbon such as toluene, xylene, cymene, and the like; a halogenated hydrocarbon such as methylene chloride, dichloroethane, and the like; an ether such as tetrahydrofuran, diisopropyl ether, and the like; a nitrile such as acetonitrile, benzonitrile, and the like; and so on. Of these, a halogenated hydrocarbon, an aromatic hydrocarbon, and a nitrile are preferable. The solvent may be used alone, or may be used in admixture of two or more kinds thereof.

In the case of using the solvent, from the viewpoints of economy and easiness in post-treatment, its use amount is preferably from 0.1 to 10 parts by mass, and more preferably from 0.1 to 5 parts by mass per part by mass of the N-hydro-β-lactam derivative (2).

Though a reaction temperature of the polymerizable group introducing step-A varies depending upon the kinds of the used polymerizable group introducing agent A, the N-hydro-β-lactam derivative (2), and the basic substance, in general, it is preferably from −50 to 80° C. Though a reaction pressure is not particularly limited, in general, the reaction is carried out at atmospheric pressure.

Also, from the viewpoint of a yield of the N-acyl-β-lactam derivative (1), it is preferable that the polymerizable group introducing step-A is carried out under an inert gas atmosphere such as nitrogen, argon, and the like.

The reaction of the polymerizable group introducing step-A can be stopped by the addition of water and/or an alcohol. As the alcohol, for example, there are preferably exemplified methanol, ethanol, n-propanol, isopropanol, and so on.

As to a use amount of water or the alcohol, it is preferable to use water or the alcohol in an amount of 1 mol or more relative to the excessive polymerizable group introducing agent A per 1 mol of the N-hydro-β-lactam derivative (2). So far as the use amount falls within this range, the excessively used polymerizable group introducing agent A can be completely decomposed, and no by-product is produced.

Specific examples of the N-acyl-β-lactam derivative (1) wherein n is 0, which can be manufactured by the polymerizable group introducing step-A, are given below, but it should not be construed that the present invention is limited thereto.

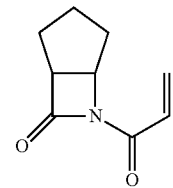

(1-1-1)

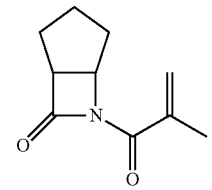

(1-1-2)

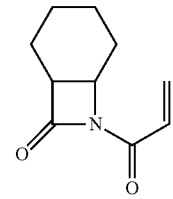

(1-1-3)

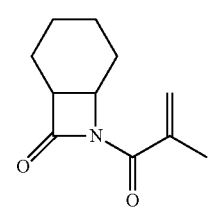

(1-1-4)

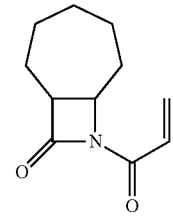

(1-1-5)

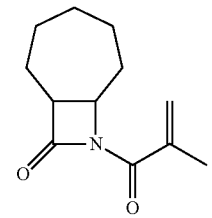

(1-1-6)

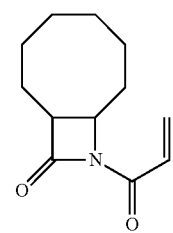

(1-1-7)

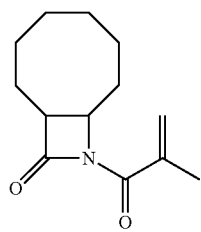
(1-1-8)
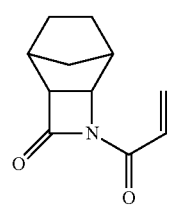
(1-1-9)
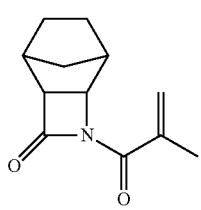
(1-1-10)
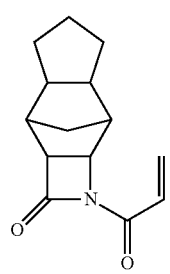
(1-1-11)
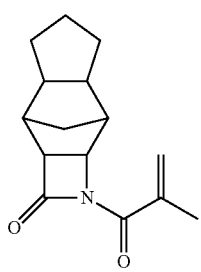
(1-1-12)
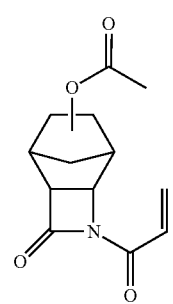
(1-1-13)
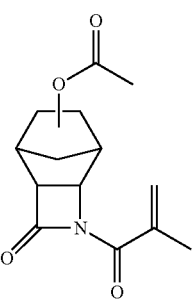
(1-1-14)
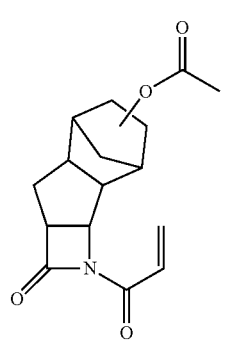
(1-1-15)
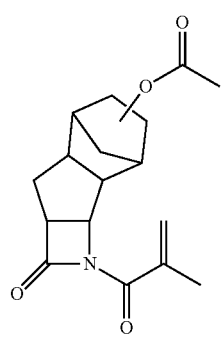
(1-1-16)
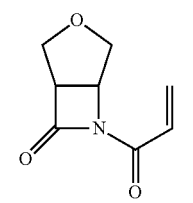
(1-1-17)
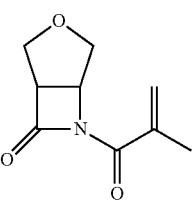
(1-1-18)
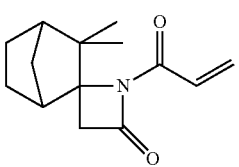
(1-2-1)

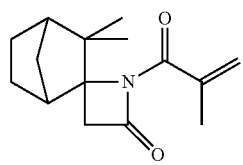 (1-2-2)
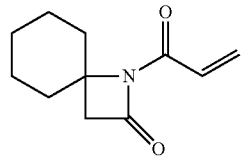 (1-2-3)
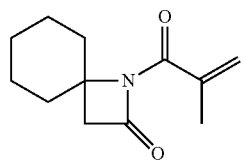 (1-2-4)
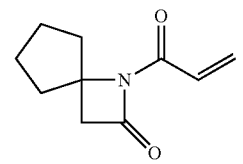 (1-2-5)
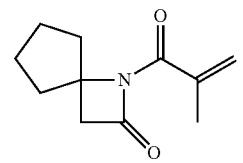 (1-2-6)
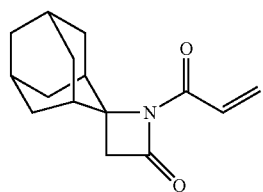 (1-2-7)
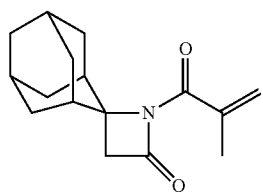 (1-2-8)
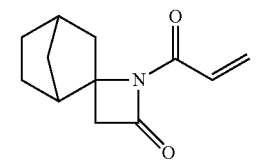 (1-2-9)
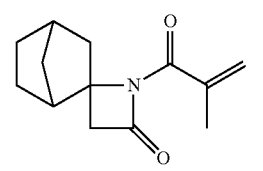 (1-2-10)
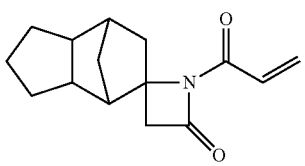 (1-2-11)
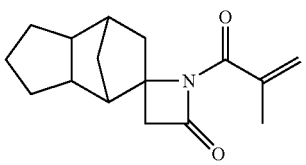 (1-2-12)
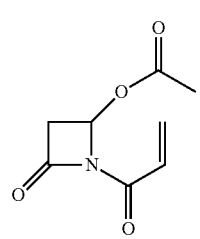 (1-3-1)
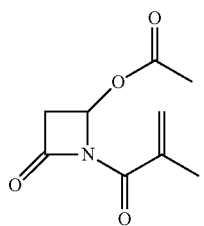 (1-3-2)
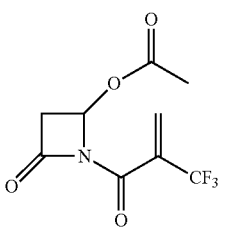 (1-3-3)
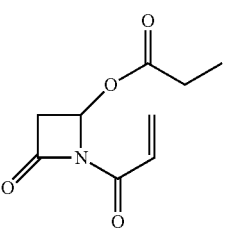 (1-3-4)
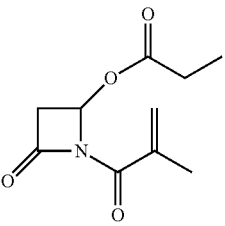 (1-3-5)

(1-3-6) 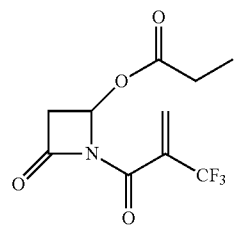
(1-3-7) 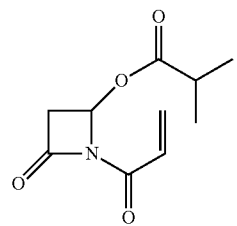
(1-3-8) 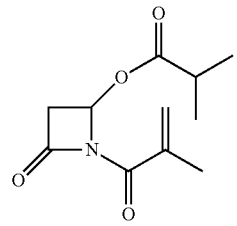
(1-3-9) 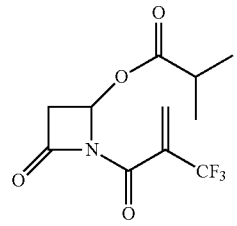
(1-3-10) 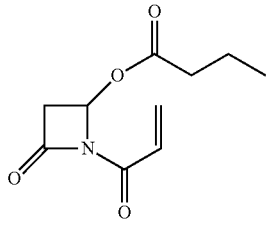
(1-3-11) 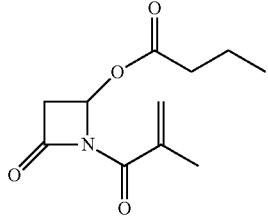
(1-3-12) 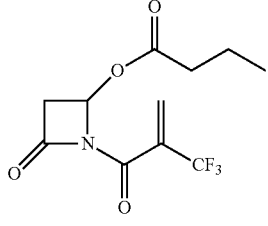
(1-3-13) 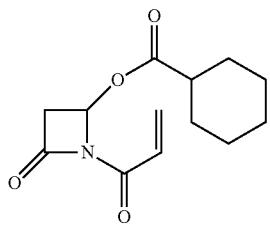
(1-3-14) 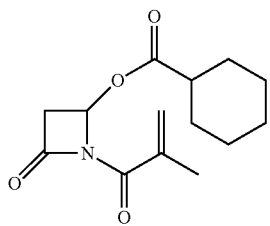
(1-3-15) 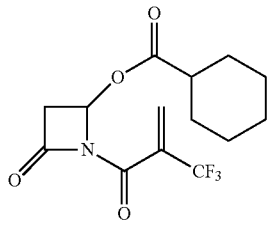
(1-3-16) 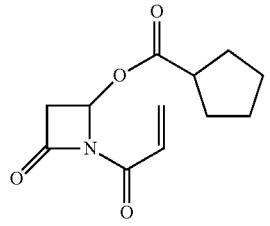
(1-3-17) 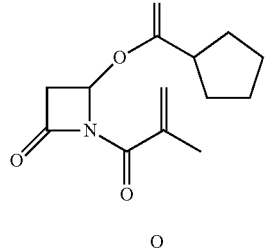
(1-3-18) 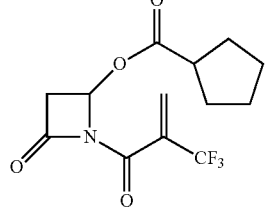
(1-3-19) 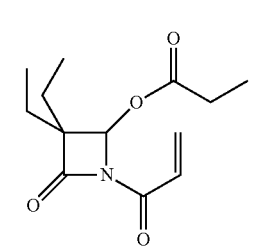

-continued

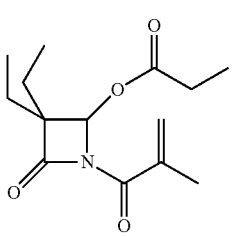
(1-3-20)

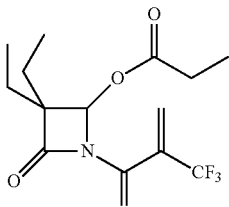
(1-3-21)

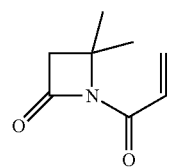
(1-4-1)

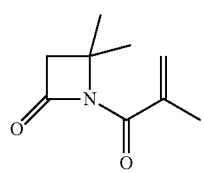
(1-4-2)

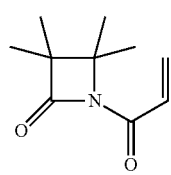
(1-4-3)

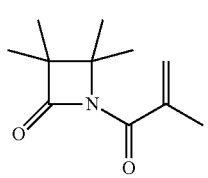
(1-4-4)

(Polymerizable Group Introducing Step-B)

Next, the polymerizable group introducing step-B is described.

—Polymerizable Group Introducing Step-B1—

Among the connecting group introducing agents B1 which are used in the polymerizable group introducing step-B1, examples of the compound represented by the formula: $X^2$—W—$COX^3$ include chloroacetyl chloride, 2-chloropropionyl chloride, 2-bromo-2-methylpropionyl bromide, and so on. Examples of the compound represented by the formula: $X^2$—W—COOC(=O)$R^8$ include chloroacetic pivalic anhydride, chloroacetic 2,4,6-trichlorobenzoic anhydride, 2-chloropropionic pivalic anhydride, 2-chloropropionic 2,4,6-trichlorobenzoic anhydride, and so on. Examples of the compound represented by the formula: $X^2$—W—COOSO$_2$$R^9$ include chloroacetic methanesulfonic anhydride, chloroacetic p-toluenesulfonic anhydride, 2-chloropropionic methanesulfonic anhydride, 2-chloropropionic p-toluenesulfonic anhydride, and so on. Examples of the compound represented by the formula $(X^2$—W—CO$)_2$O include chloroacetic anhydride, 2-chloropropionic anhydride, and so on.

Though a use amount of the connecting group introducing agent B1 is not particularly limited, from the viewpoints of economy and easiness in post-treatment, it is preferably from 0.8 to 5 mol, and more preferably from 0.8 to 3 mol per 1 mol of the N-hydro-β-lactam derivative (2).

Examples of the basic substance which is used in the polymerizable group introducing step-B1 include the same substances as those in the basic substance which is used in the polymerizable group introducing step-A.

Though a use amount of the basic substance is not particularly limited, from the viewpoints of economy and easiness in post-treatment, it is preferably from 0.8 to 5 mol, and more preferably from 0.8 to 3 mol per 1 mol of the N-hydro-β-lactam derivative (2).

The polymerizable group introducing step-B1 is carried out in the presence or absence of a solvent.

The solvent is not particularly limited so far as it does not inhibit the reaction, and examples thereof include the same solvents as those which can be used in the polymerizable group introducing step-A. The solvent may be used alone, or may be used in admixture of two or more kinds thereof.

In the case of using the solvent, from the viewpoints of economy and easiness in post-treatment, its use amount is preferably from 0.1 to 10 parts by mass, and more preferably from 0.1 to 5 parts by mass per part by mass of the N-hydro-β-lactam derivative (2).

Though a reaction temperature of the polymerizable group introducing step-B1 varies depending upon the kinds of the used connecting group introducing agent B1, the N-hydro-β-lactam derivative (2), and the basic substance, in general, it is preferably from −50 to 80° C. Though a reaction pressure of the polymerizable group introducing step-B1 is not particularly limited, in general, the reaction is carried out at atmospheric pressure.

Also, from the viewpoint of a yield of the desired compound, it is preferable that the polymerizable group introducing step-B1 is carried out under an inert gas atmosphere such as nitrogen, argon, and the like.

The reaction of the polymerizable group introducing step-B1 can be stopped by the addition of water and/or an alcohol. As the alcohol, for example, there are preferably exemplified methanol, ethanol, n-propanol, isopropanol, and so on.

As to a use amount of water or the alcohol, it is preferable to use water or the alcohol in an amount of 1 mol or more relative to the excessive connecting group introducing agent B1 per 1 mol of the N-hydro-β-lactam derivative (2). So far as the use amount falls within this range, the excessively used connecting group introducing agent B1 can be completely decomposed, and no by-product is produced.

—Polymerizable Group Introducing Step-B2—

Examples of the polymerizable group introducing agent B2 which is used in the polymerizable group introducing step-B2 include sodium acrylate, potassium acrylate, sodium methacrylate, potassium methacrylate, and the like. As a preparation method thereof, from the viewpoint of simplicity of the operations, a method of preparing the polymerizable group introducing agent B2 by allowing acrylic acid or methacrylic acid to react with a base such as sodium hydroxide, sodium carbonate, potassium hydroxide, potassium carbonate, and the like in a reaction system is preferable.

From the viewpoints of economy and easiness in post-treatment, a use amount of the polymerizable group introducing agent B2 is preferably from 0.8 to 5 mol, and more preferably from 0.8 to 3 mol per 1 mol of the product of the polymerizable group introducing step-B1.

In the polymerizable group introducing step-B2, if desired, it is preferable to use, as an activating agent, potassium iodide, sodium iodide, tetrabutylammonium iodide, tetrabutylammonium bromide, or the like.

In the case of using the activating agent, its use amount is preferably from 0.001 to 0.5 mol, and from the viewpoints of easiness in post-treatment and economy, its use amount is more preferably from 0.005 to 0.3 mol per 1 mol of the product of the polymerizable group introducing step-B1.

The polymerizable group introducing step-B2 is carried out in the presence or absence of a solvent.

The solvent is not particularly limited so far as it does not inhibit the reaction. Examples thereof include an aliphatic hydrocarbon such as hexane, heptane, octane, and the like; an aromatic hydrocarbon such as toluene, xylene, cymene, and the like; a halogenated hydrocarbon such as methylene chloride, dichloroethane, and the like; an ether such as tetrahydrofuran, diisopropyl ether, and the like; and an amide such as N,N-dimethylformamide, N,N-dimethylacetamide, N-methylpyrrolidone, and the like. The solvent may be used alone, or may be used in admixture of two or more kinds thereof.

In the case of using the solvent, from the viewpoints of economy and easiness in post-treatment, its use amount is preferably from 0.1 to 10 parts by mass, and more preferably from 0.1 to 5 parts by mass per part by mass of the product of the polymerizable group introducing step-B1.

Though a reaction temperature of the polymerizable group introducing step-B2 varies depending upon the kinds of the used polymerizable group introducing agent B2, the product of the polymerizable group introducing step-B1, and the basic substance, in general, it is preferably from −50 to 80° C. Though a reaction pressure is not particularly limited, in general, the reaction is carried out at atmospheric pressure.

Specific examples of the N-acyl-β-lactam derivative (1) wherein n is 1, which can be manufactured by the polymerizable group introducing step-B, are given below, but it should not be construed that the present invention is limited thereto.

(1-1-19)

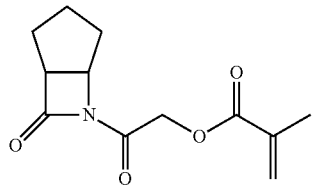

(1-1-20)

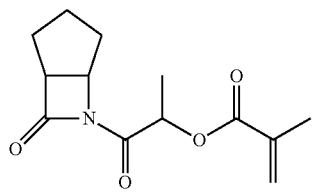

(1-1-21)

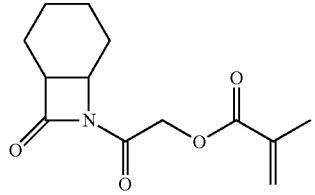

(1-1-22)

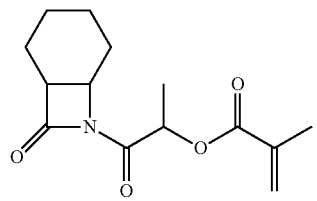

(1-1-23)

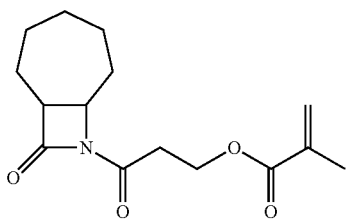

(1-1-24)

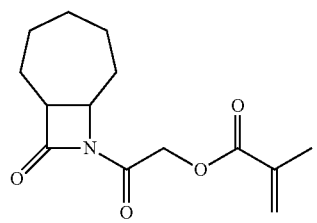

(1-1-25)

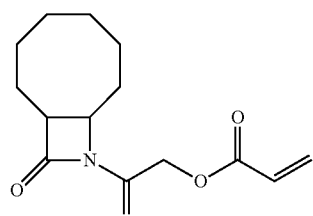

(1-1-26)

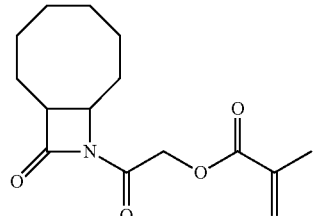

(1-1-27)

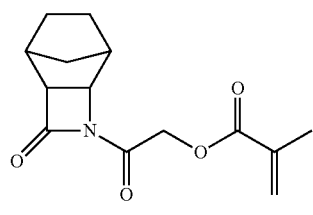

(1-1-28)

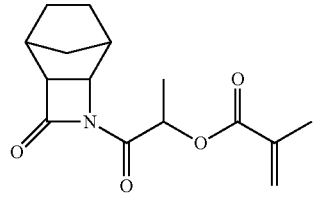

(1-1-29)
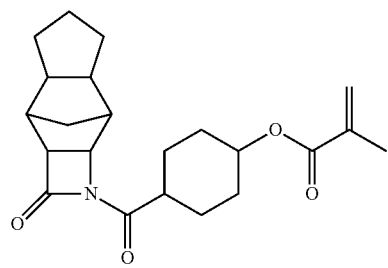
(1-1-30)
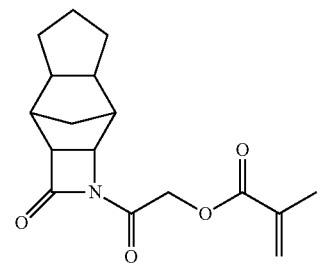
(1-1-31)
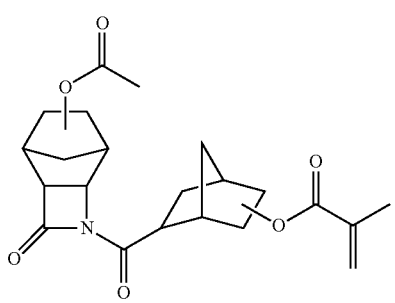
(1-1-32)
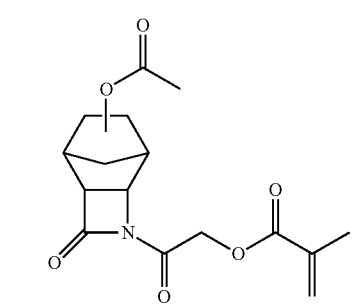
(1-1-33)
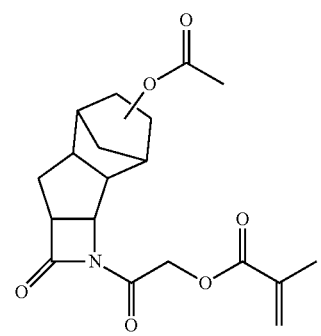
(1-1-34)
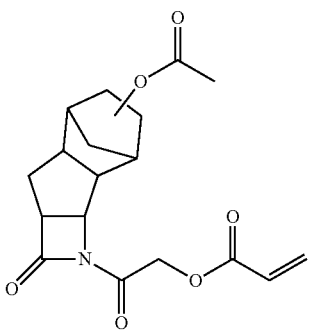
(1-1-35)
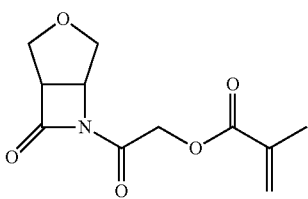
(1-1-36)
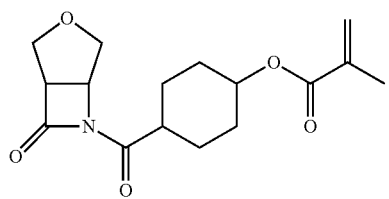
(1-2-13)
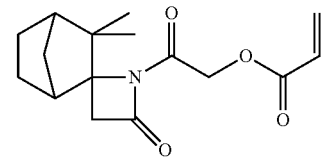
(1-2-14)
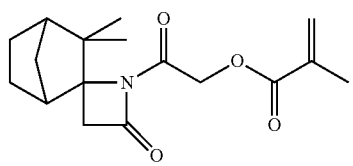
(1-2-15)
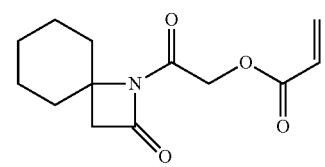
(1-2-16)
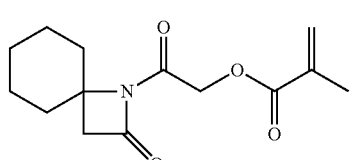
(1-2-17)

(1-2-18)
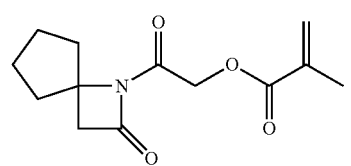
(1-2-19)
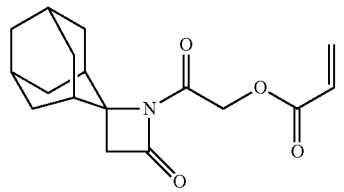
(1-2-20)
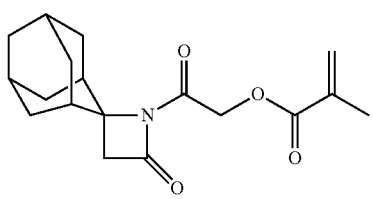
(1-2-21)
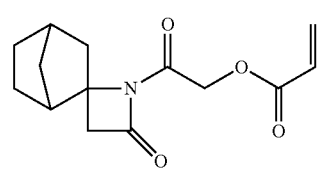
(1-2-22)
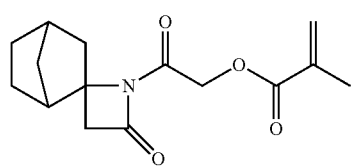
(1-2-23)
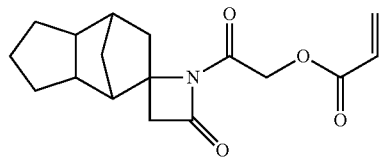
(1-2-24)
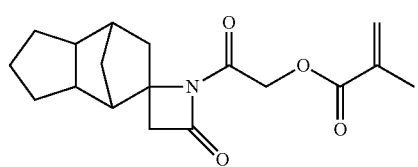
(1-3-22)
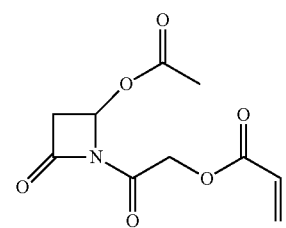
(1-3-23)
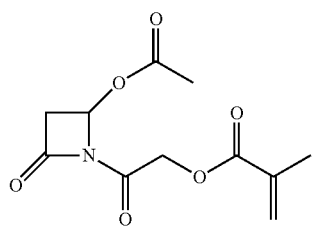
(1-3-24)
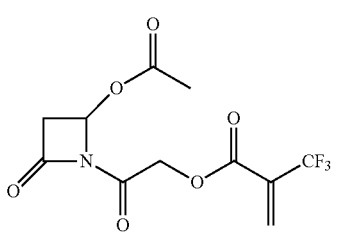
(1-3-25)
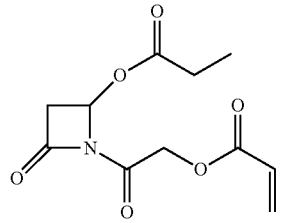
(1-3-26)
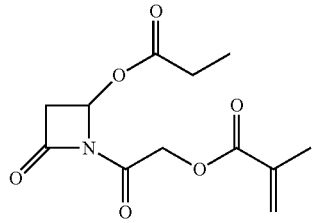
(1-3-27)
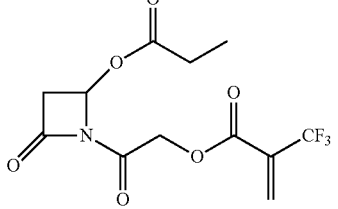
(1-3-28)
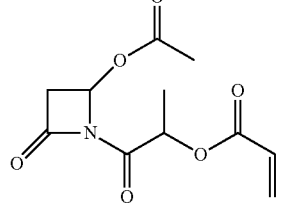
(1-3-29)

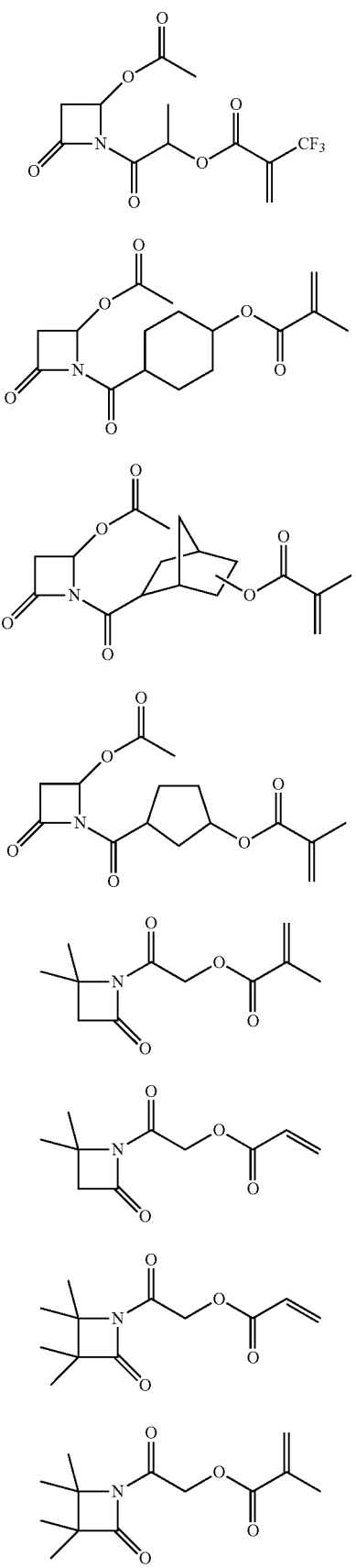

(1-3-30)
(1-3-31)
(1-3-32)
(1-3-33)
(1-4-5)
(1-4-6)
(1-4-7)
(1-4-8)

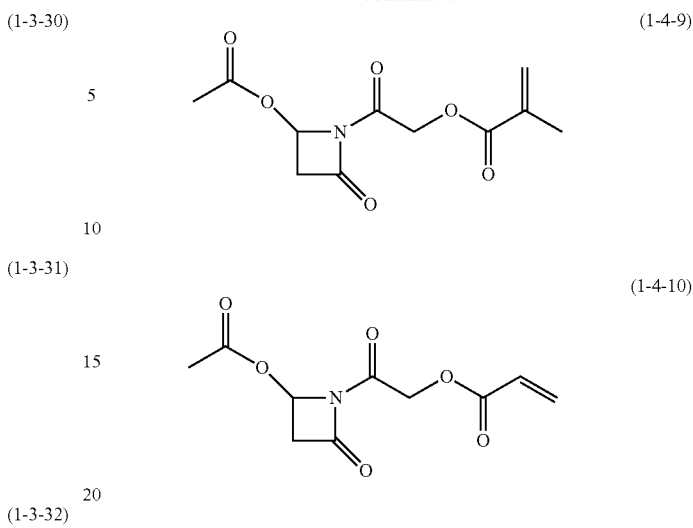

(1-4-9)
(1-4-10)

If desired, it is preferable that the N-acyl-β-lactam derivative (1) obtained through the polymerizable group introducing step-A or the polymerizable group introducing step-B is separated and purified in the usual way.

For example, after the reaction mixture obtained by the polymerizable group introducing step-A or the polymerizable group introducing step-B is washed with water and then concentrated, the N-acyl-β-lactam derivative (1) can be separated and purified by a method which is used for usual separation and purification of an organic compound, such as distillation, column chromatography, recrystallization, and the like.

Also, if desired, it is possible to reduce a content of metals of the obtained N-acyl-β-lactam derivative (1) by adding a chelating agent such as nitrilotriacetate, ethylenediaminetetraacetic acid, and the like, followed by filtration or a treatment with a metal-removing filter such as Zeta Plus (a trade name, manufactured by Cuno Inc.), Protego (a trade name, manufactured by Nihon Mykrolis Ltd.), and the like.

Incidentally, the starting N-hydro-β-lactam derivative (2) can be manufactured by allowing a corresponding olefin compound to react with chlorosulfonyl isocyanate and then hydrolyzing the chlorosulfonyl group in the presence of a reducing agent such as sodium sulfite, sodium hydrogensulfite, and the like.

[Polymer]

The polymer of the present invention is one obtained by polymerizing the foregoing N-acyl-β-lactam derivative (1) alone or one obtained by copolymerizing the N-acyl-β-lactam derivative (1) with other polymerizable compound. The "other polymerizable compound" as referred to herein is a compound from which "other constituent unit" as described later is derived.

The polymer of the present invention contains a constituent unit on the basis of the N-acyl-β-lactam derivative (1) (hereinafter referred to as "constituent unit (1')") in an amount of more than 0% by mole and up to 100% by mole, and from the viewpoint of a reduction of LWR, in an amount of preferably from 10 to 80% by mole, more preferably from 20 to 70% by mole, and still more preferably from 20 to 60% by mole.

Specific examples of the constituent unit (1') are given below, but it should not be construed that the present invention is limited thereto.

(1'-1-1)
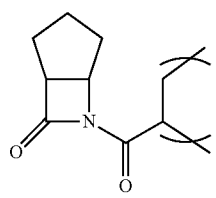
(1'-1-2)
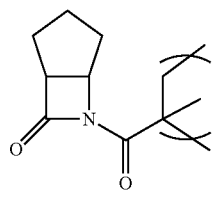
(1'-1-3)
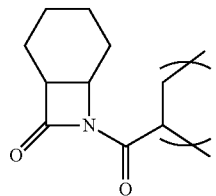
(1'-1-4)
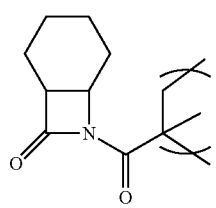
(1'-1-5)
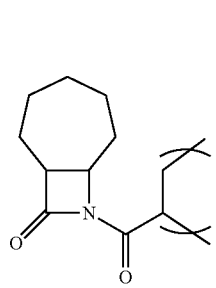
(1'-1-6)
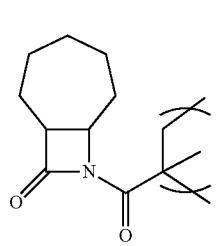
(1'-1-7)
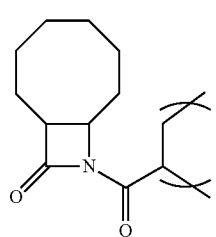
-continued
(1'-1-8)
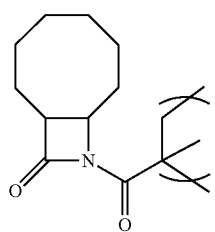
(1'-1-9)
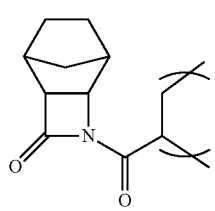
(1'-1-10)
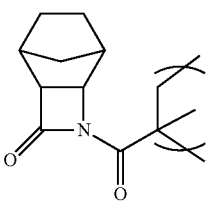
(1'-1-11)
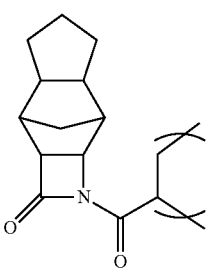
(1'-1-12)
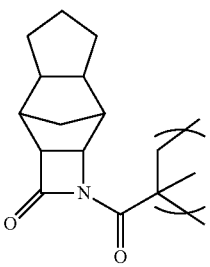
(1'-1-13)
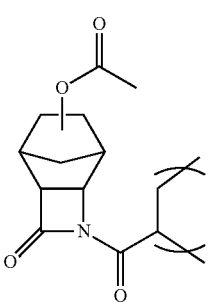

(1'-1-14) 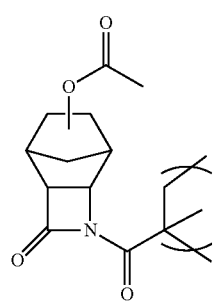
(1'-1-15) 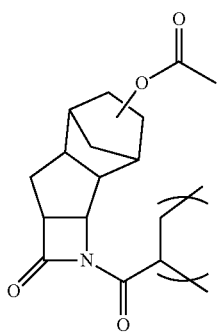
(1'-1-16) 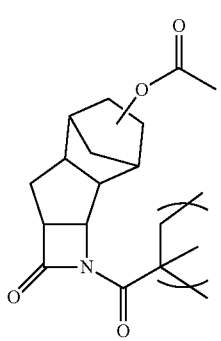
(1'-1-17) 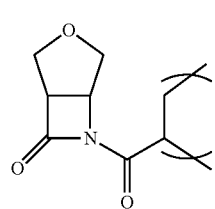
(1'-1-18) 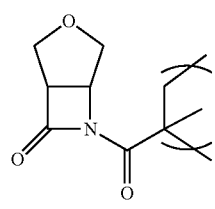
(1'-1-19) 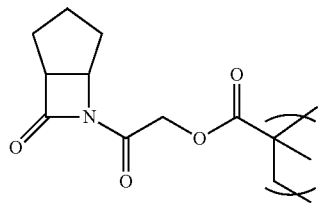
(1'-1-20) 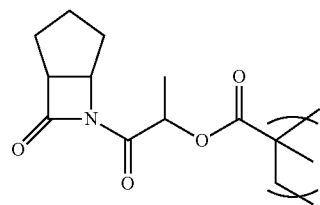
(1'-1-21) 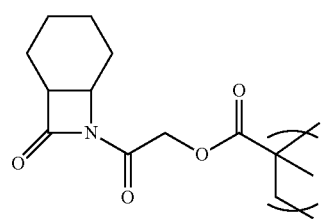
(1'-1-22) 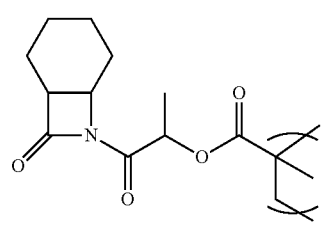
(1'-1-23) 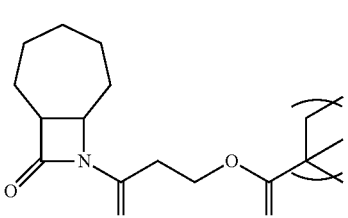
(1'-1-24) 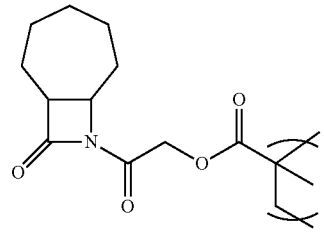
(1'-1-25) 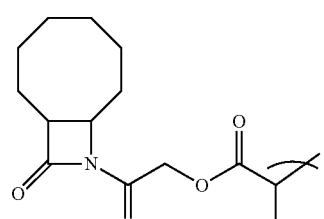
(1'-1-26) 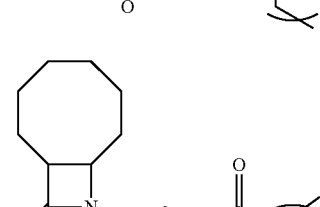

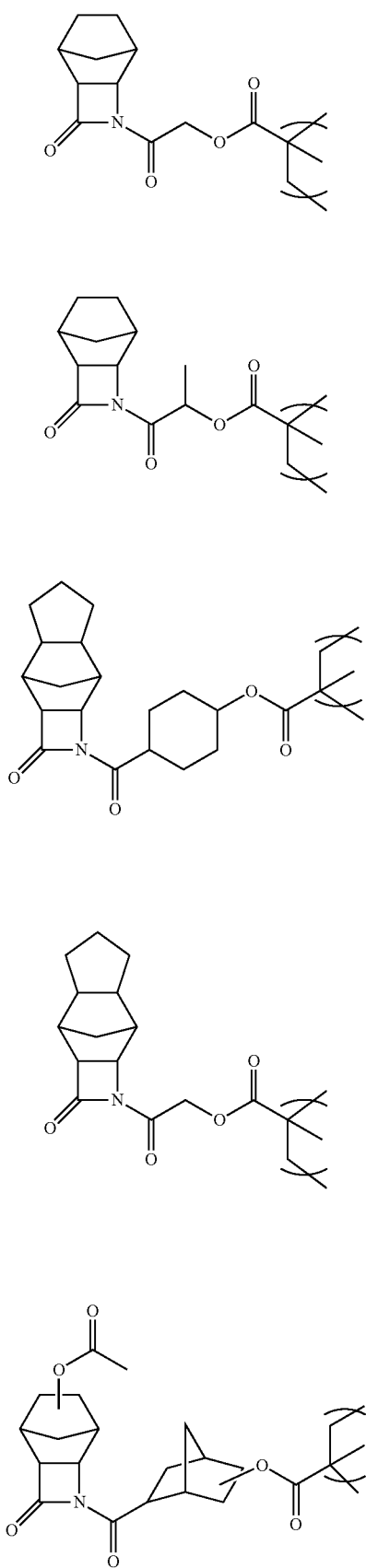
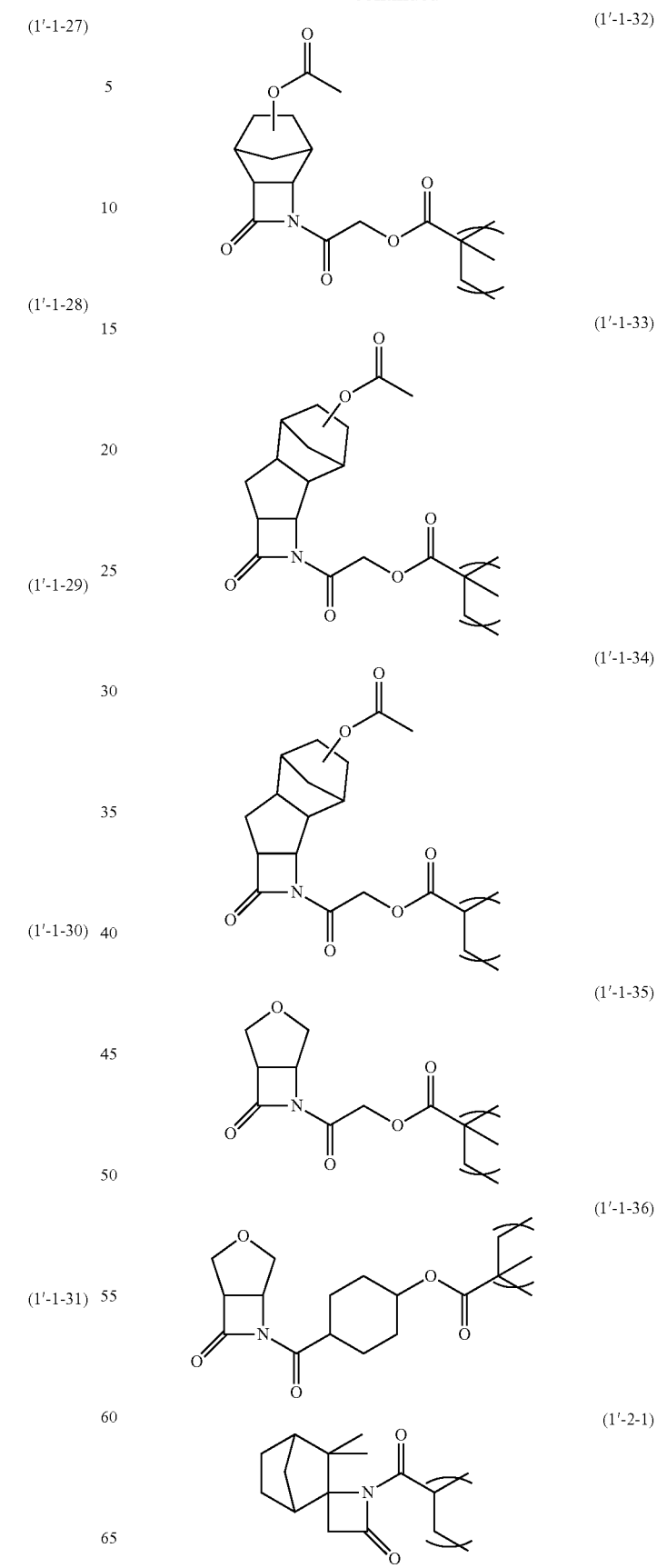

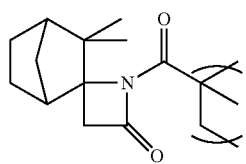 (1'-2-2)
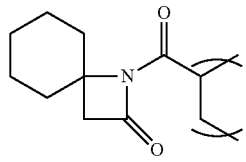 (1'-2-3)
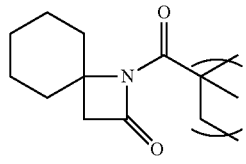 (1'-2-4)
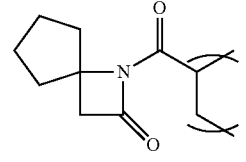 (1'-2-5)
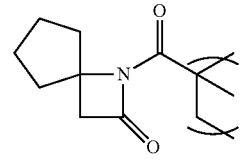 (1'-2-6)
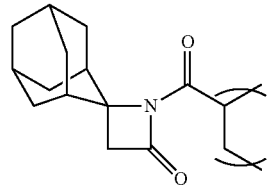 (1'-2-7)
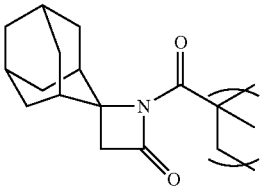 (1'-2-8)
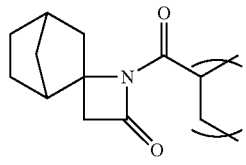 (1'-2-9)
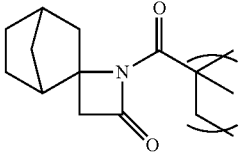 (1'-2-10)
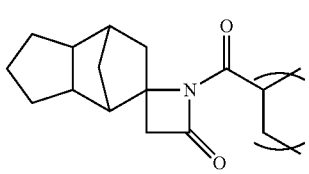 (1'-2-11)
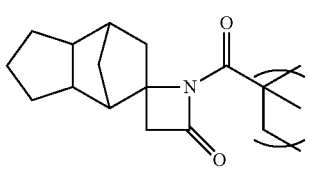 (1'-2-12)
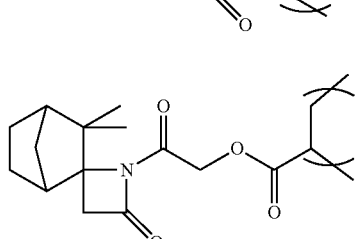 (1'-2-13)
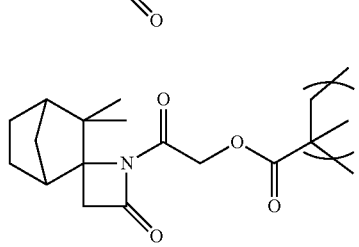 (1'-2-14)
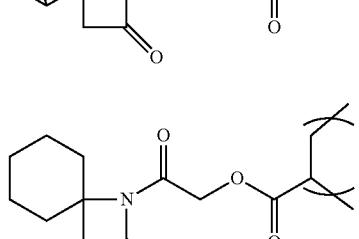 (1'-2-15)
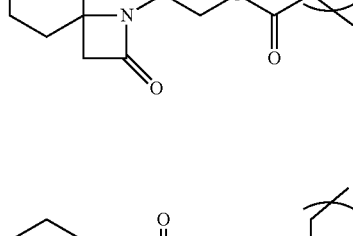 (1'-2-16)
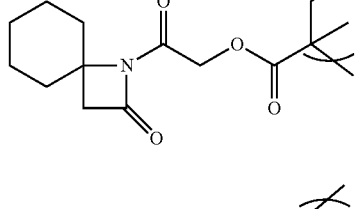 (1'-2-17)
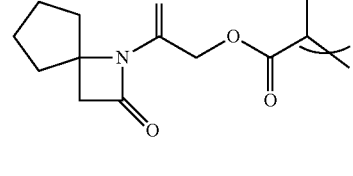 (1'-2-18)
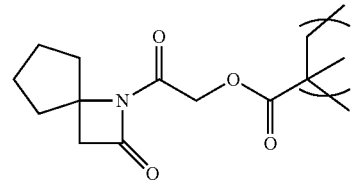

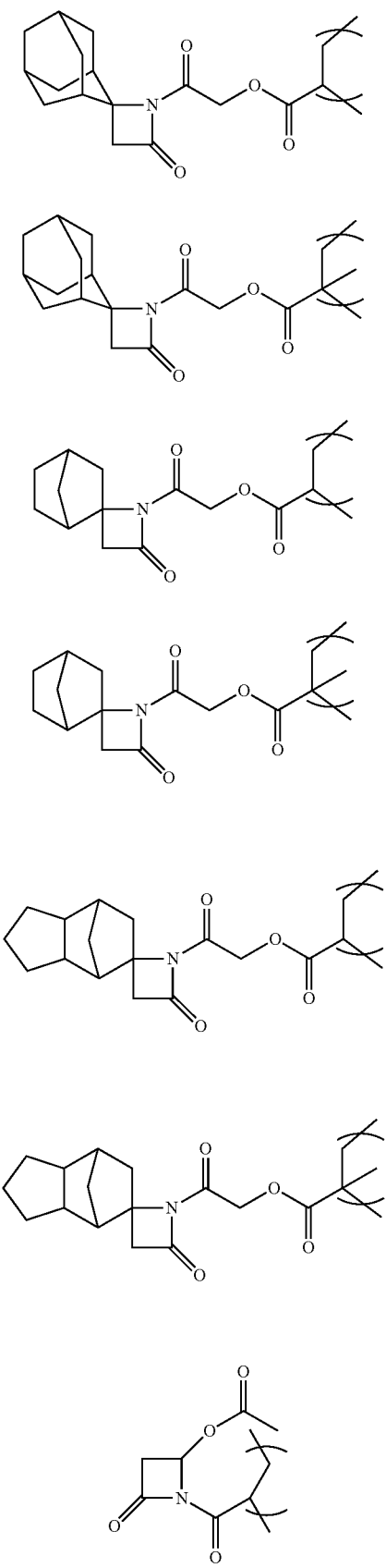
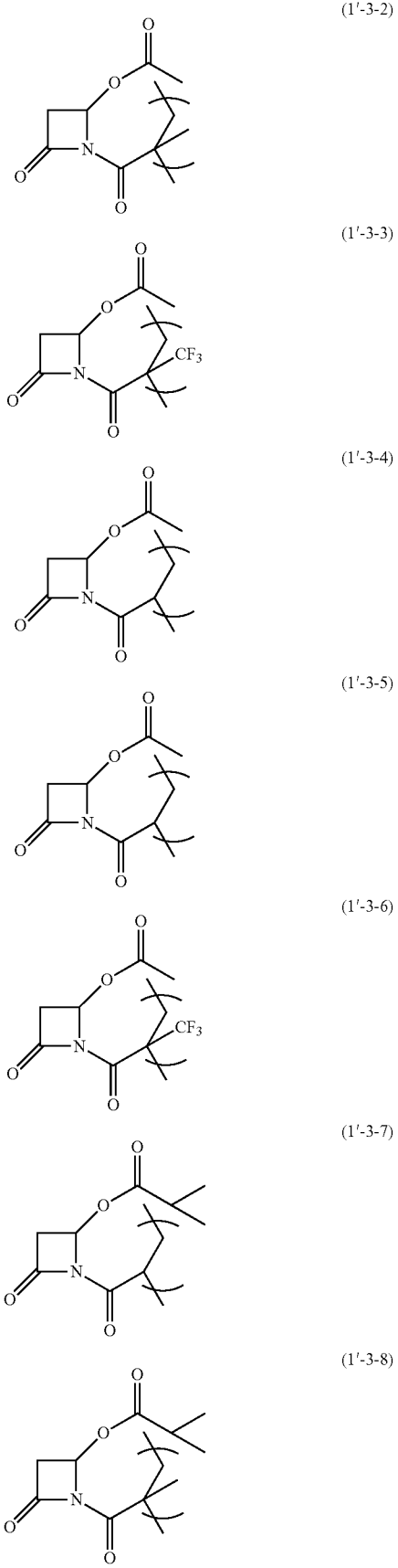

(1'-3-9) 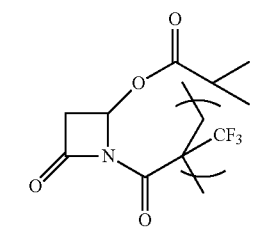
(1'-3-10) 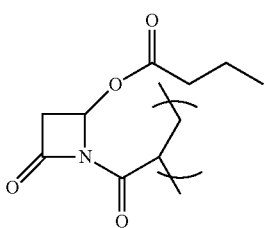
(1'-3-11) 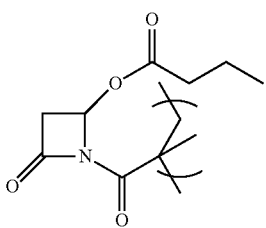
(1'-3-12) 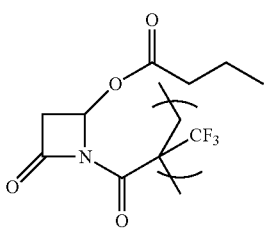
(1'-3-13) 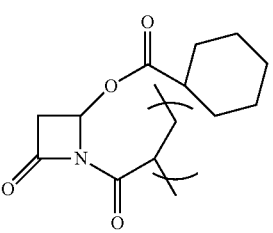
(1'-3-14) 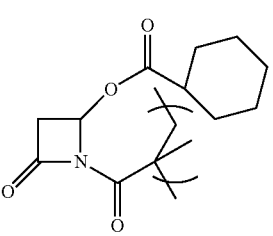
(1'-3-15) 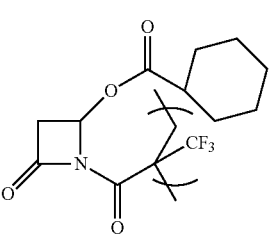
(1'-3-16) 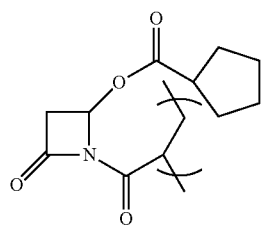
(1'-3-17) 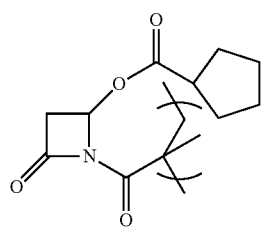
(1'-3-18) 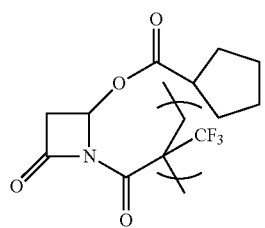
(1'-3-19) 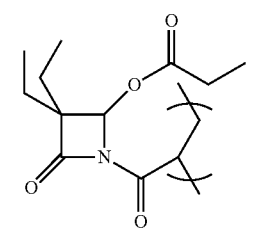
(1'-3-20) 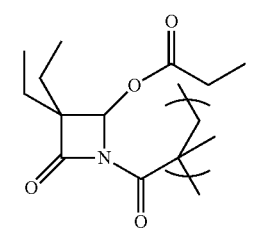
(1'-3-21) 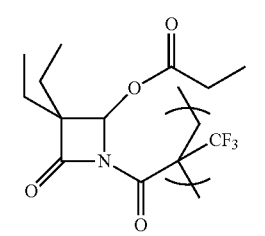
(1'-3-22) 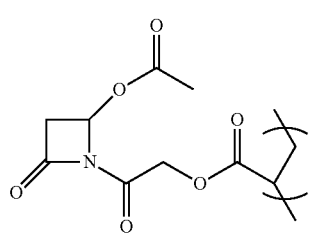

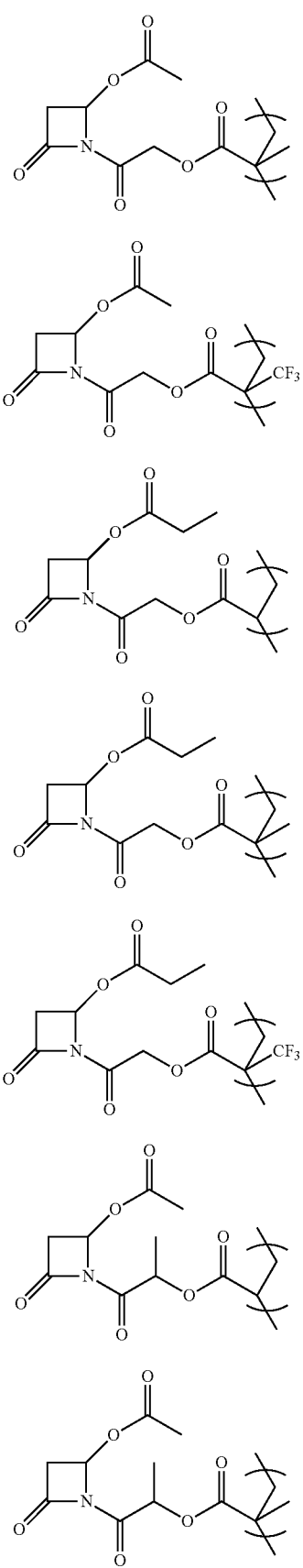
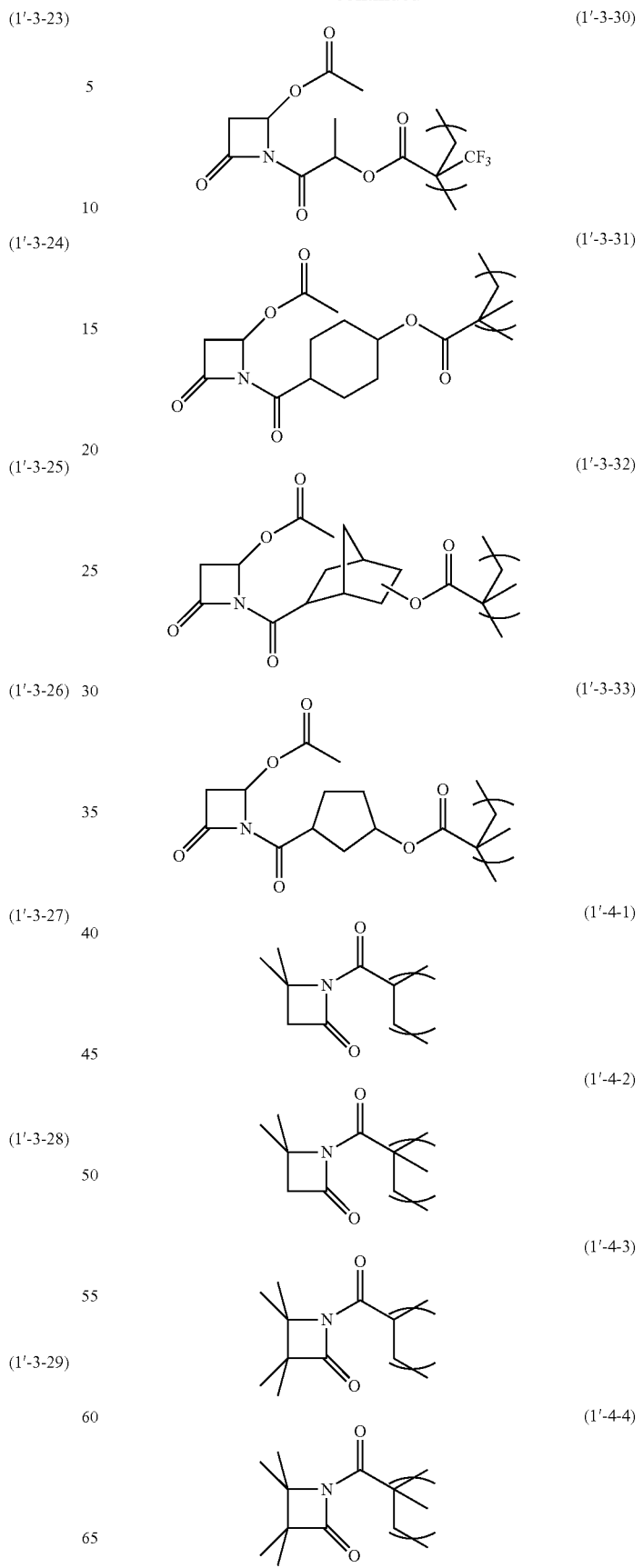

(1'-4-5)
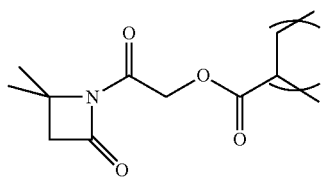

(1'-4-6)
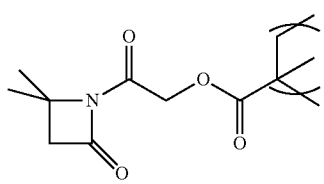

(1'-4-7)
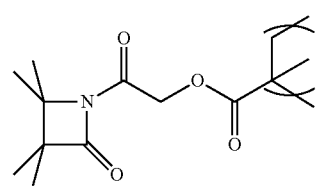

(1'-4-8)
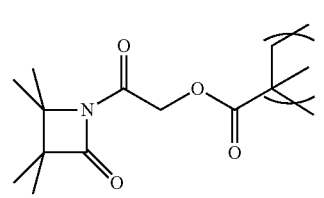

Examples of the constituent unit on the basis of the foregoing other polymerizable compound include constituent units (a1) to (a5) as described below, and the constituent unit is properly chosen depending upon an application of the resist composition, desired properties, and the like.

(Constituent Unit (a1))

The constituent unit (a1) is a constituent unit which is derived from an acid dissociable dissolution inhibiting group-containing acrylic ester. The acid dissociable dissolution inhibiting group is one which in forming a resist pattern as the resist composition, not only has alkali dissolution inhibiting properties so as to make the whole of the polymer sparingly soluble in an alkaline developing solution prior to the dissociation but is dissociated by an acid generated from the acid generator component upon exposure, thereby increasing the solubility of the whole of this polymer in an alkaline developing solution.

Though such a constituent unit (a1) is not particularly limited, examples thereof include the following structural units (a1-1) to (a1-49).

(a1-1)
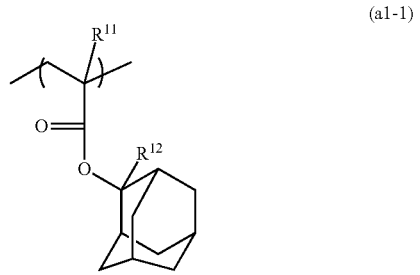

(a1-2)
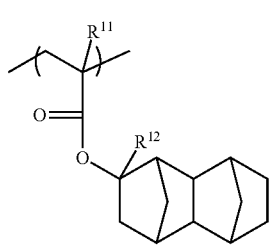

(a1-3)
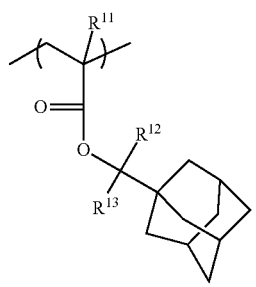

(a1-4)
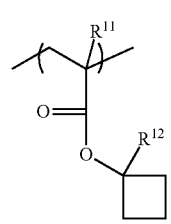

(a1-5)
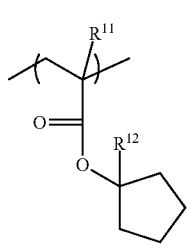

(a1-6)
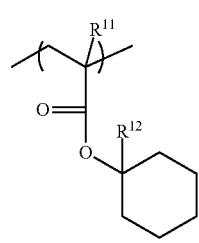

(a1-7)
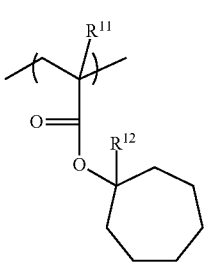

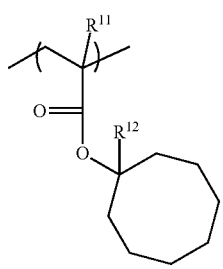 (a1-8)
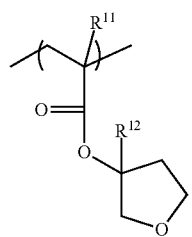 (a1-9)
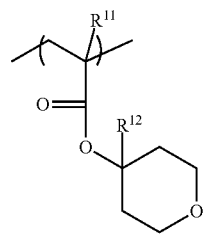 (a1-10)
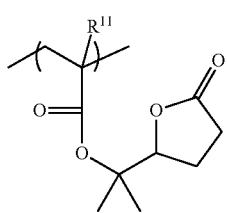 (a1-11)
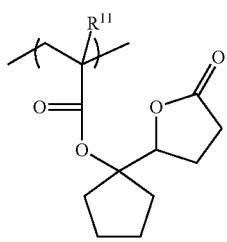 (a1-12)
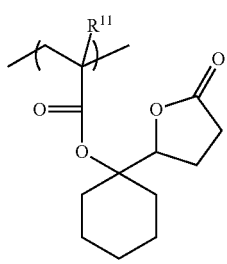 (a1-13)
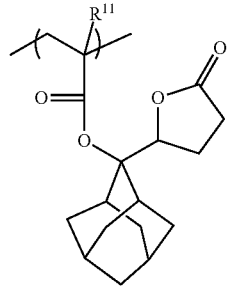 (a1-14)
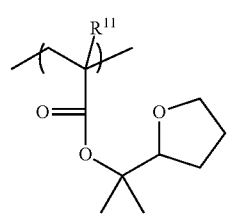 (a1-15)
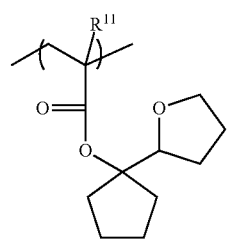 (a1-16)
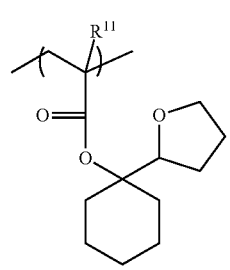 (a1-17)
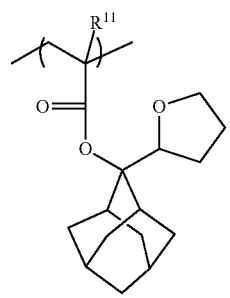 (a1-18)
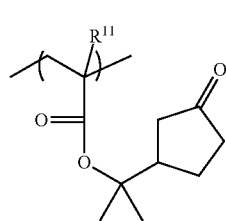 (a1-19)

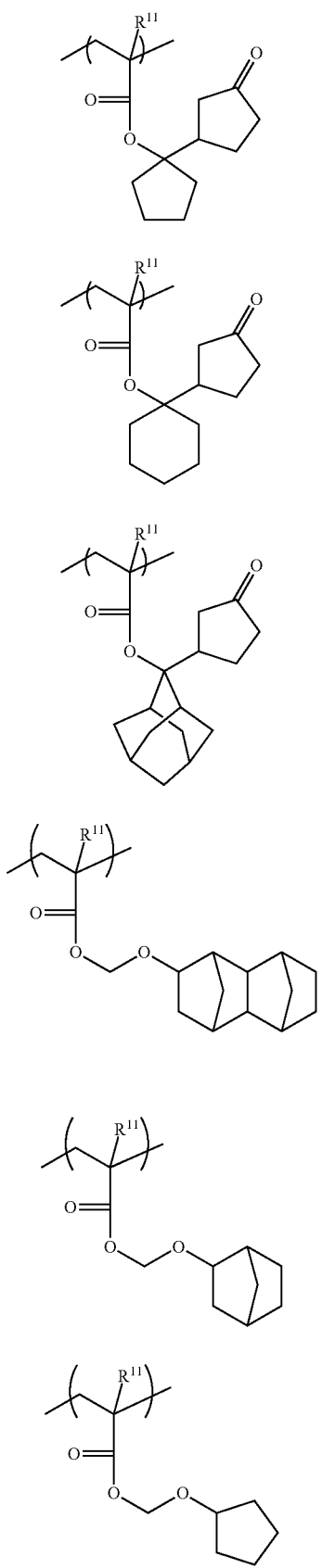
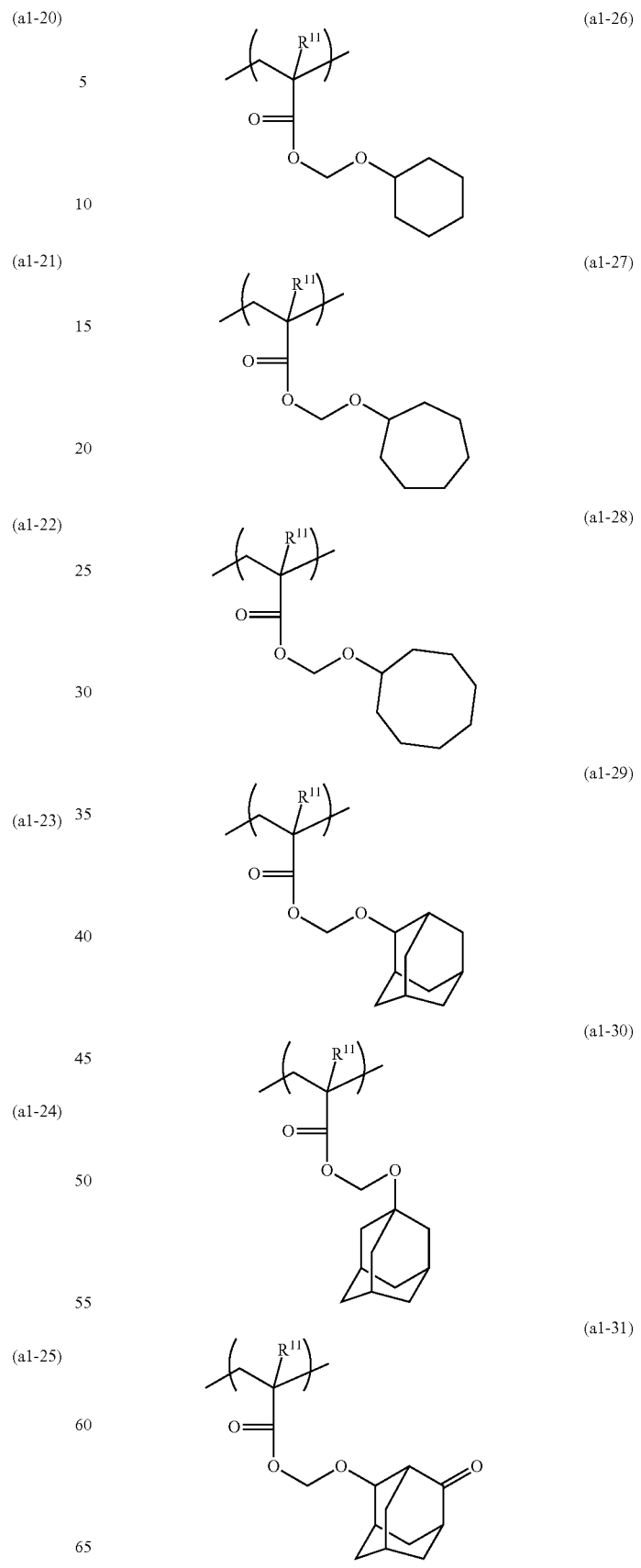

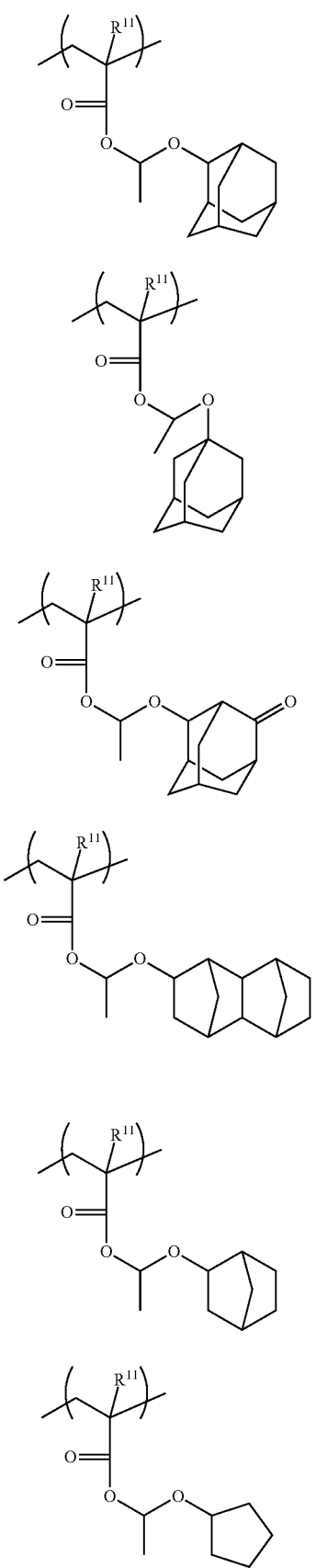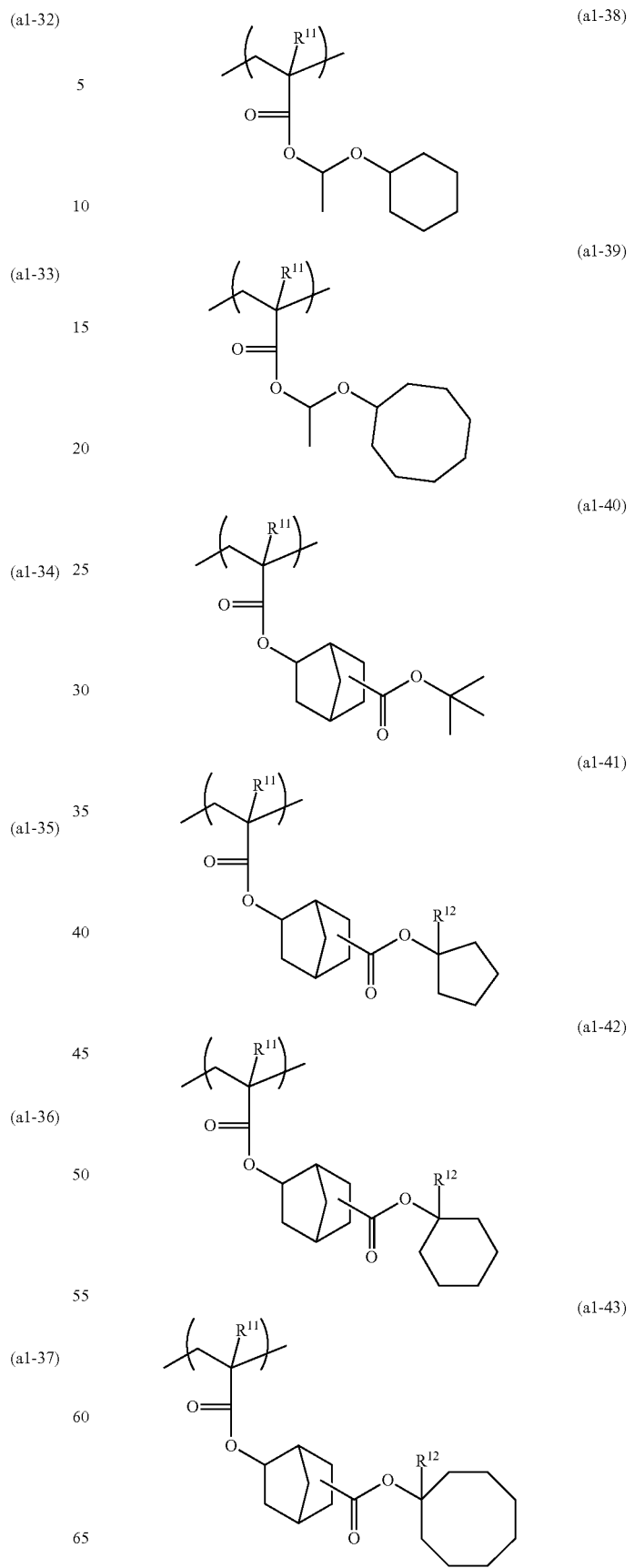

-continued (a1-44)
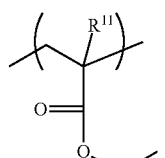

(a1-45)
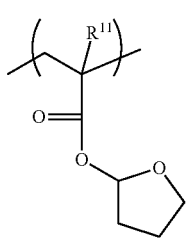

(a1-46)
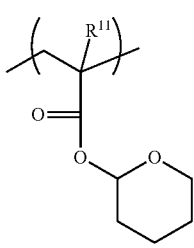

(a1-47)
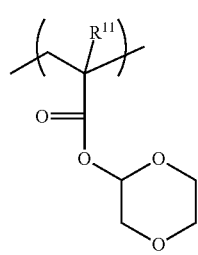

(a1-48)
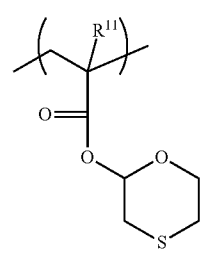

(a1-49)
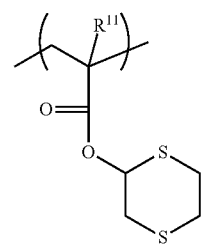

In the foregoing constituent units (a1-1) to (a1-49), $R^{11}$ represents a hydrogen atom or a halogenated or non-halogenated alkyl group having a carbon number of from 1 to 5; and each of $R^{12}$ and $R^{13}$ independently represents an alkyl group having a carbon number of from 1 to 10.

Examples of the halogenated or non-halogenated alkyl group having a carbon number of from 1 to 5, which $R^{11}$ represents, include a methyl group, a trifluoromethyl group, an ethyl group, a pentafluoroethyl group, various propyl groups (it is meant by the term "various" that a linear group and all of branched groups are included; hereinafter the same), various butyl groups, and so on. Incidentally, $R^{11}$ is preferably a hydrogen atom or a methyl group.

Examples of the alkyl group having a carbon number of from 1 to 10, which each of $R^{12}$ and $R^{13}$ independently represents, include a methyl group, an ethyl group, various propyl groups, various butyl groups, various hexyl groups, various octyl groups, various decyl groups, and so on. Of these, an alkyl group having a carbon number of from 1 to 5 is preferable, and a methyl group and an ethyl group are more preferable.

Among the foregoing constituent units (a1-1) to (a1-49), from the viewpoint of an improving effect of LWR, (a1-1) is preferable.

The foregoing constituent unit (a1) may be composed of only one kind, or may be composed of two or more kinds thereof.

In the case where the polymer has the constituent unit (a1), though a proportion of the constituent unit (a1) is not particularly limited, from the standpoints of sensitivity, resolution and adhesion to a substrate of the resist film, it is preferably from 10 to 80% by mole, and more preferably from 20 to 70% by mole in the whole of the constituent units constituting the polymer of the present invention. When the proportion of the constituent unit (a1) falls within this range, at the time of forming a resist composition, a pattern can be easily obtained, and a balance with other constituent units can be taken.

(Constituent Unit (a2))

The constituent unit (a2) is a constituent unit which is derived from an acrylic ester having a lactone-containing group. The lactone-containing group as referred to herein means a group containing one lactone ring containing a —O—C(O)— structure. In this specification, with respect to the ester group of the foregoing acrylic ester, the ester group having only a lactone ring as the cyclic compound is referred to as "monocyclic group", and in the case of further having other cyclic structure, the ester group is referred to as "polycyclic group" regardless of a structure thereof.

In the case of using the polymer for the formation of a resist film, the lactone-containing group of the constituent unit (a2) is effective for enhancing the adhesion of the resist film to a substrate or enhancing the affinity with a water-containing developing solution.

Examples of the lactone-containing monocyclic group include a group obtained by eliminating one hydrogen atom from γ-butyrolactone. Examples of the lactone-containing polycyclic group include a group obtained by eliminating one hydrogen atom from a lactone ring-containing bicycloalkane, tricycloalkane or tetracycloalkane.

More specific examples of the constituent unit (a2) include the following constituent units (a2-1) to (a2-6), but it should not be construed that the present invention is limited thereto.

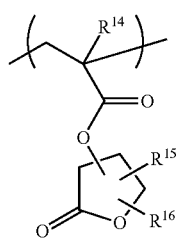

(a2-1)

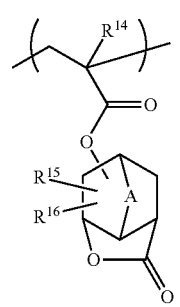

(a2-2)

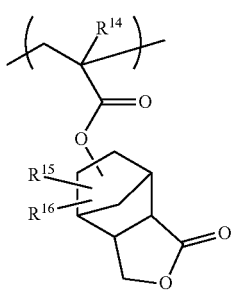

(a2-3)

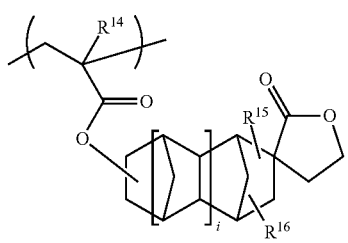

(a2-4)

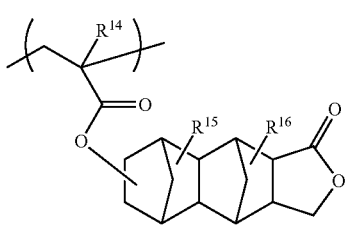

(a2-5)

-continued

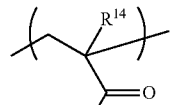

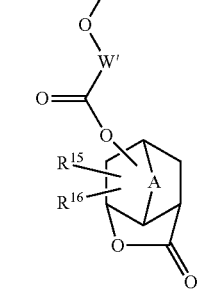

(a2-6)

In the formulae, $R^{14}$ represents a hydrogen atom or a halogenated or non-halogenated alkyl group having a carbon number of from 1 to 5. Each of $R^{15}$ and $R^{16}$ independently represents a hydrogen atom, an alkyl group having a carbon number of from 1 to 5, an alkoxy group having a carbon number of from 1 to 5, or —COOR$^{17}$ ($R^{17}$ is an alkyl group having a carbon number of from 1 to 3). W' represents an alkylene group having a carbon number of from 1 to 10 or a cycloalkylene group having a carbon number of from 3 to 10. A represents an alkylene group having a carbon number of from 1 to 5 or an oxygen atom. Also, represents 0 or 1.

Examples of the halogenated or non-halogenated alkyl group having a carbon number of 1 to 5, which $R^{14}$ represents, include the same groups as those in the case of $R^{11}$. Of these, a methyl group, an ethyl group, and a trifluoromethyl group are preferable, with a methyl group and an ethyl group being more preferable.

Examples of the alkyl group having a carbon number of from 1 to 5, which each of $R^{15}$ and $R^{16}$ independently represents, include a methyl group, an ethyl group, various propyl groups, and various butyl groups. Of these, a methyl group and an ethyl group are preferable. —COOR$^{17}$ is preferably —COOCH$_3$.

Incidentally, from the viewpoint of easiness in industrial availability, it is preferable that all of $R^{15}$ and $R^{16}$ are a hydrogen atom (namely, no special substituent is present on the foregoing constituent unit).

The alkylene group having a carbon number of from 1 to 10, which W represents, may be either linear or branched. Examples of the alkylene group include a methylene group, an ethylene group, a propylene group, a trimethylene group, and so on. Examples of the cycloalkylene group having a carbon number of from 3 to 10 include a cyclopentane-diyl group, a cyclohexane-diyl group, and so on.

Examples of the alkylene group having a carbon number of from 1 to 5, which A represents, include a methylene group, a 1,2-ethylene group, a 1,1-ethylene group, an isopropylene group, and so on.

Specific examples of the foregoing constituents (a2-1) to (a2-6) are given below in succession, but it should not be construed that the present invention is limited thereto.

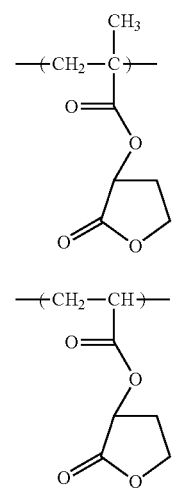
(a2-1-1)
(a2-1-2)
(a2-1-3)
(a2-1-4)
(a2-1-5)
(a2-1-6)
-continued
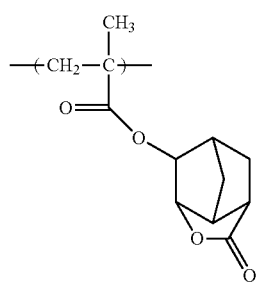
(a2-2-1)
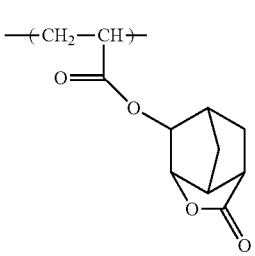
(a2-2-2)
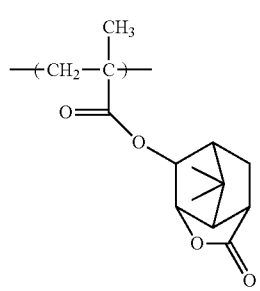
(a2-2-3)
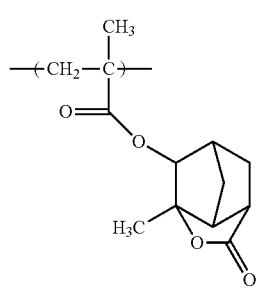
(a2-2-4)
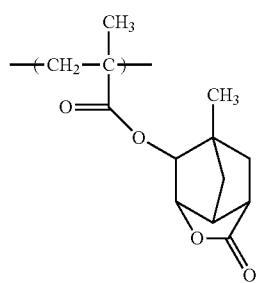
(a2-2-5)

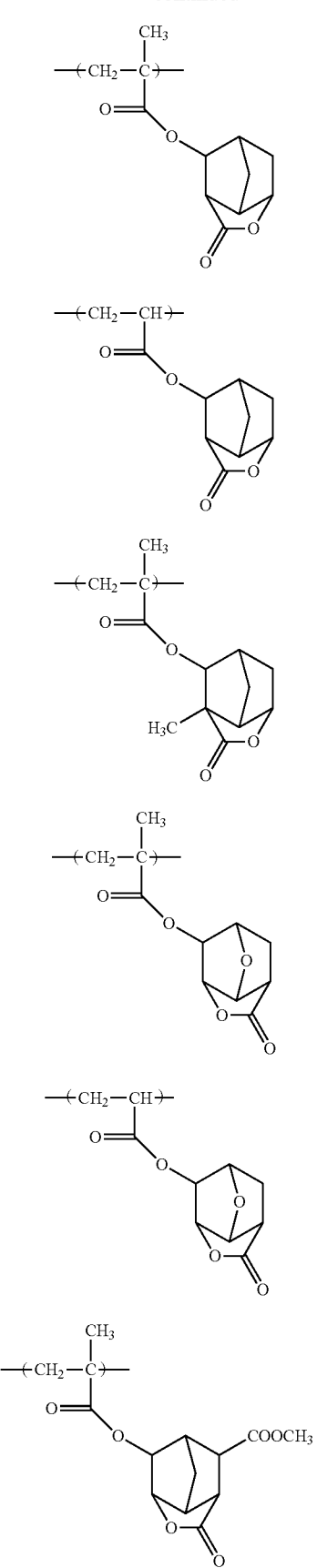
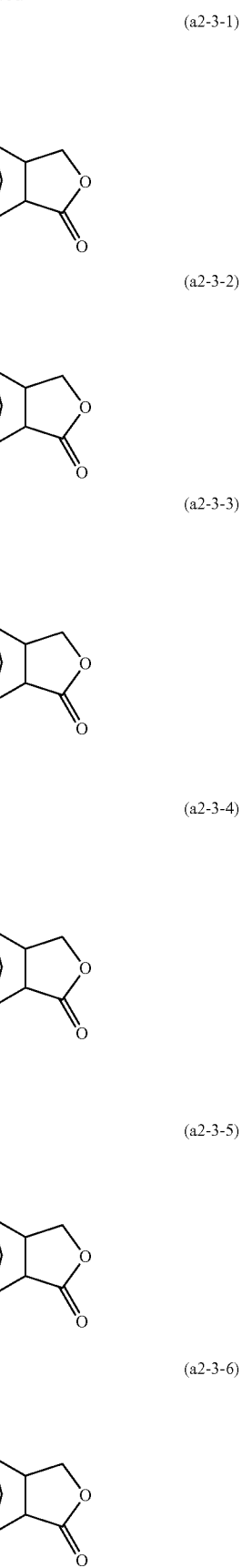

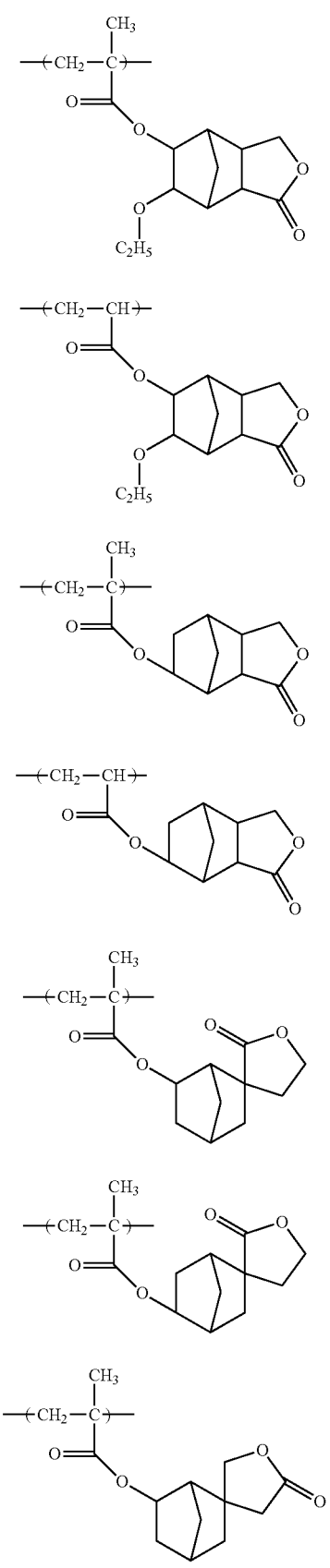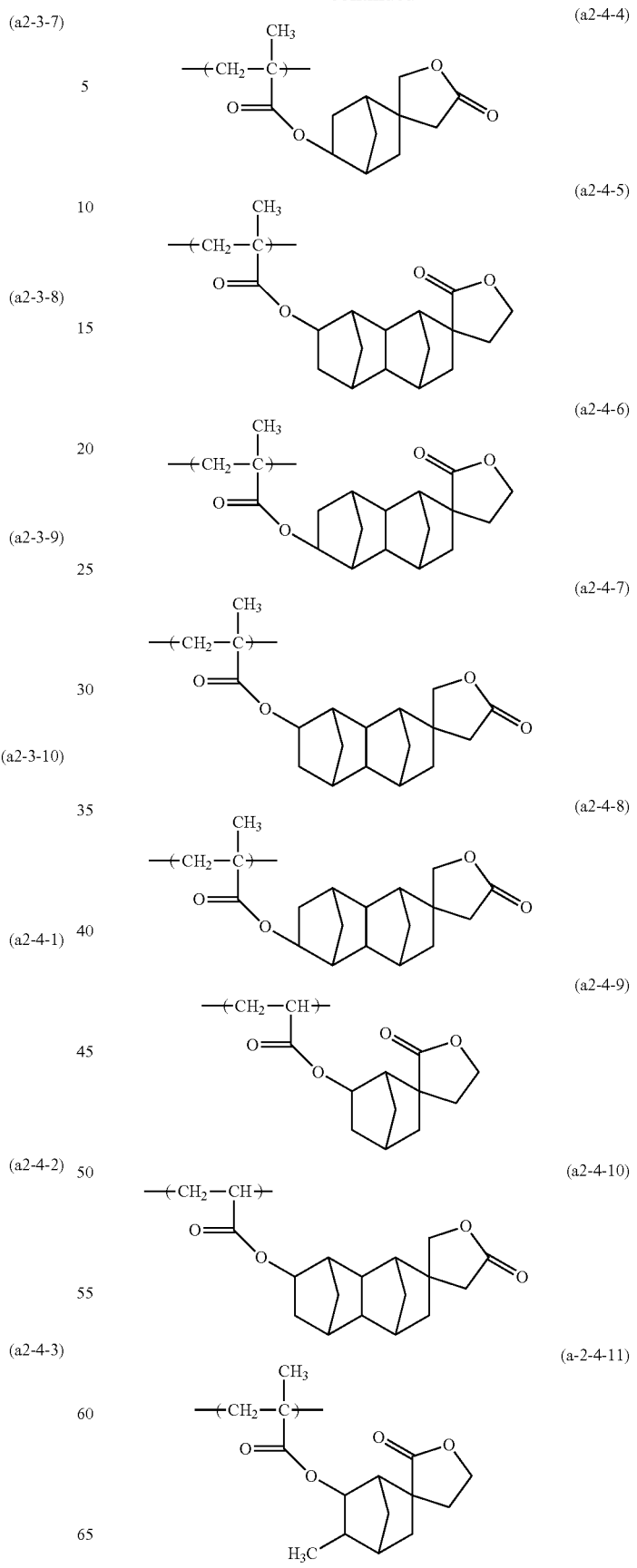

(a2-4-12)
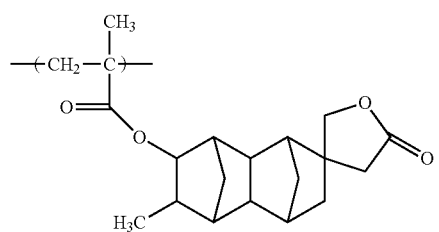
(a-2-5-1)
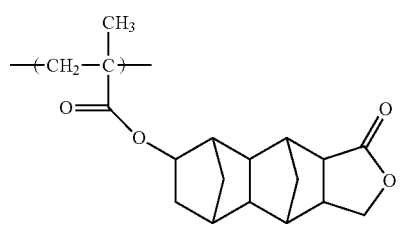
(a2-5-2)
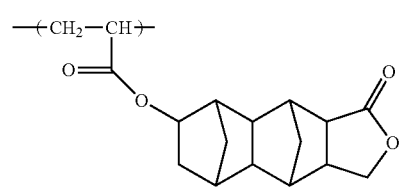
(a2-5-3)
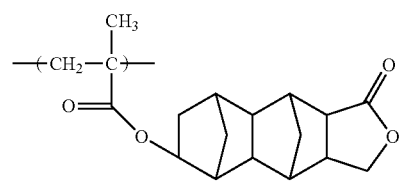
(a2-5-4)
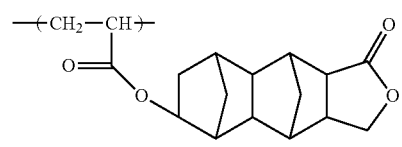
(a2-5-5)
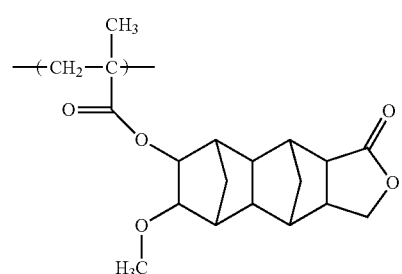
(a2-5-6)
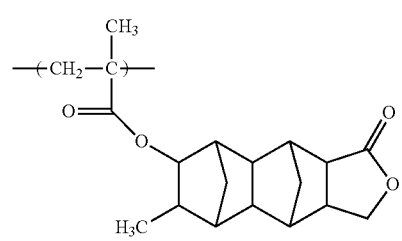
(a2-6-1)
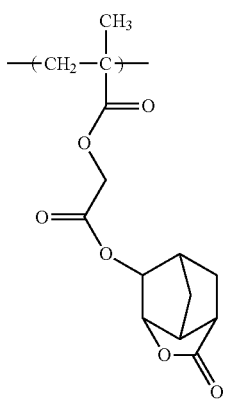
(a2-6-2)
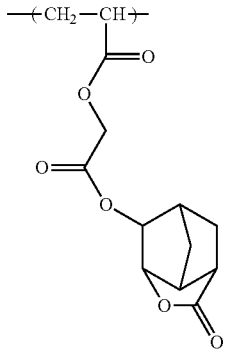
(a2-6-3)
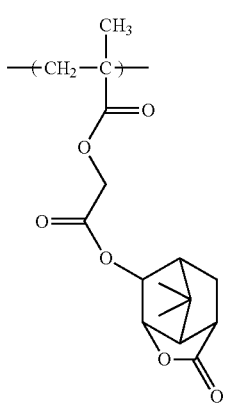
(a2-6-4)
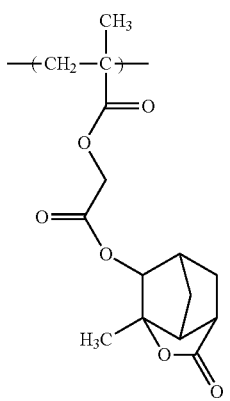

(a2-6-5) 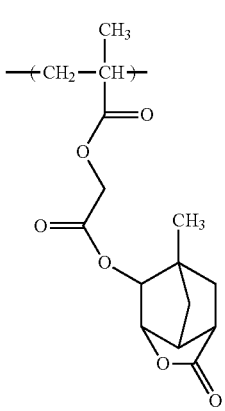

(a2-6-6) 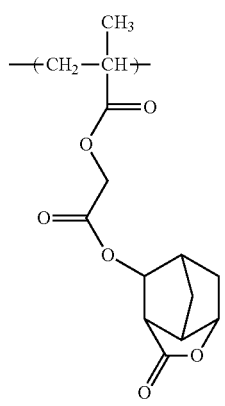

(a2-6-7) 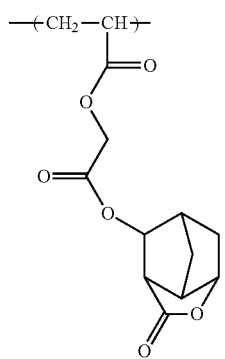

(a2-6-8) 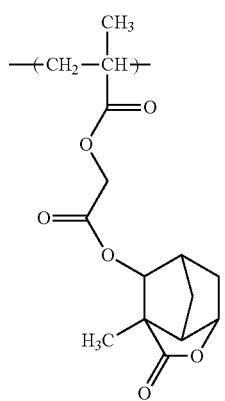

(a2-6-9) 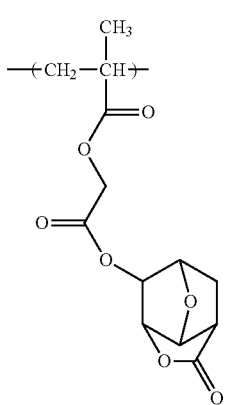

(a2-6-10) 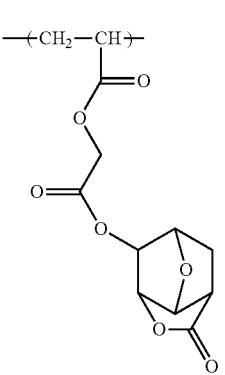

(a2-6-11) 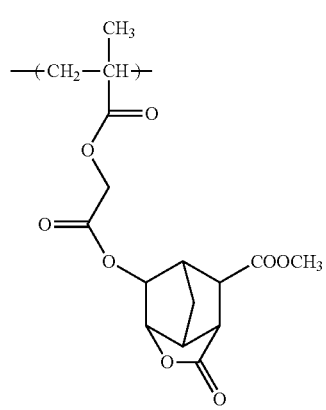

The foregoing constituent unit (a2) may be composed of only one kind, or may be composed of two or more kinds thereof.

The constituent unit (a2) is preferably composed of at least one member selected from the group consisting of the foregoing constituent units (a2-1) to (a2-6), and preferably composed of at least one member selected from the general formulae (a2-1) to (a2-3). More specifically, the constituent unit (a2) is preferably composed of at least one member selected from the group consisting of the constituent units (a2-1-1), (a2-1-2), (a2-2-1), (a2-2-2), (a2-3-1), (a2-3-2), (a2-3-9) and (a2-3-10).

In the case where the polymer has the constituent unit (a2), a proportion of the constituent unit (a2) is preferably from 1 to 60% by mole, more preferably from 10 to 55% by mole, and still more preferably from 20 to 55% by mole relative to the whole of the constituent units constituting the polymer of the present invention. When the proportion of the constituent unit (a2) falls within this range, the effects to be brought by incorporating the constituent unit (a2) are sufficiently obtained, and a balance with other constituent units can be taken.

(Constituent Unit (a3))

The constituent unit (a3) is a constituent unit which is derived from an acrylic ester having a polar group-containing aliphatic hydrocarbon group. By the fact that the polymer has the constituent unit (a3), the hydrophilicity of the polymer is enhanced; and at the time of forming a positive working resist pattern by using a polymer for a base material component of a positive working resist composition, the affinity with the developing solution (alkaline aqueous solution) is enhanced, and the alkali solubility in an exposed area is enhanced, thereby contributing to an enhancement of the resolution.

Examples of the polar group include a hydroxyl group, a cyano group, a carboxyl group, and so on. Of these, a hydroxyl group is preferable. The polar group which the polar group-containing aliphatic hydrocarbon group has may be one kind or two or more kinds thereof.

As the preferred constituent unit (a3), there are exemplified the following constituent units (3') and (a3'') and so on.

The constituent unit (a3') is a constituent unit which is derived from an acrylic ester having a hydroxyl group-containing alicyclic hydrocarbon group. The "hydroxyl group-containing alicyclic hydrocarbon group" as referred to herein is a group in which a hydroxyl group is bonded to an alicyclic hydrocarbon group. The hydroxyl group may be bonded directly to the aliphatic ring, or may be bonded indirectly to the aliphatic ring as, for example, a hydroxyalkyloxy group.

The alkyl group in the hydroxyalkyloxy group is preferably linear or branched. A carbon number of the alkyl group is preferably from 2 to 5, more preferably from 2 to 4, and still more preferably 2 or 3. A hydroxyl group number in the hydroxyalkyloxy group is preferably from 1 to 4, more preferably from 1 to 3, and still more preferably 1 or 2. The hydroxyl group is more preferably a primary hydroxyl group or a secondary hydroxyl group, and still more preferably a primary hydroxyl group.

The hydroxyalkyloxy group is preferably a monohydroxyalkyloxy group or a dihydroxyalkyloxy group; and more preferably a monohydroxyethyloxy group, a monohydroxypropyloxy group, or a dihydroxypropyloxy group.

A number of a hydroxyl group or groups bonded to the alicyclic hydrocarbon group is preferably from 1 to 3, and more preferably 1. The alicyclic hydrocarbon group may have a substituent, or may be unsubstituted. Examples of the substituent include an alkyl group having a carbon number of from 1 to 5, a fluorine atom, a fluorine atom-substituted fluorinated alkyl group having a carbon number of from 1 to 5, an oxygen atom (=O), and so on.

In the alicyclic hydrocarbon group, a part of carbon atoms constituting the ring may be substituted with a hetero atom such as an oxygen atom, a nitrogen atom, a sulfur atom, and the like.

Though the alicyclic hydrocarbon group may be either saturated or unsaturated, from the standpoints of high transparency to an ArF excimer laser, etc. and excellent resolution or depth of focus (DOF), etc., it is preferably saturated.

Though the alicyclic hydrocarbon group may be a monocyclic group or a polycyclic group, it is preferably a polycyclic group. Also, a carbon number of the alicyclic hydrocarbon group is preferably from 5 to 15.

Specific examples of the alicyclic hydrocarbon group (the moiety from which the hydroxyl group or groups have been removed) in the hydroxyl group-containing alicyclic hydrocarbon group include the following. As the monocyclic group, there are exemplified a group obtained by eliminating two or more hydrogen atoms from a cycloalkane, and so on.

More specifically, there is exemplified a group obtained by eliminating two or more hydrogen atoms from cyclopentane or cyclohexane, and a group obtained by eliminating two hydrogen atoms from cyclohexane is preferable.

As the polycyclic group, there are exemplified a group obtained by eliminating two or more hydrogen atoms from a bicycloalkane, a tricycloalkane, a tetracycloalkane, or the like, and so on. More specifically, there are exemplified a group obtained by eliminating two or more hydrogen atoms from a polycycloalkane such as adamantane, norbornane, isobornane, tricyclodecane, tetracyclododecane, and the like, and so on.

Of these, from the viewpoint of easiness in industrial availability, a group obtained by eliminating two hydrogen atoms from cyclohexane, adamantane, norbornane, or tetracyclododecane is preferable, with a group obtained by eliminating two hydrogen atoms from adamantane or norbornane being more preferable.

In the constituent unit (a3'), it is preferable that the hydroxyl group-containing alicyclic hydrocarbon group is bonded to an oxygen atom of an end of a carbonyloxy group [—C(O)—O—] of an acrylic ester.

As a preferred specific example of the constituent unit (a3'), for example, there is exemplified the following constituent unit (a3'-1).

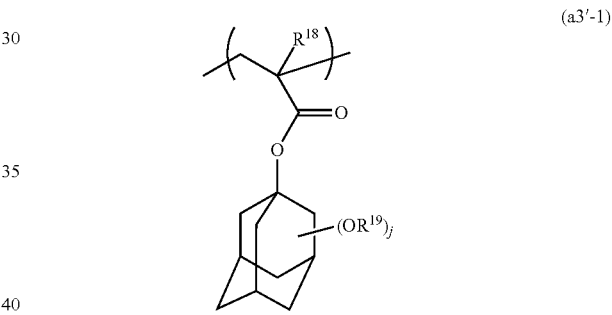

(a3'-1)

In the foregoing constituent unit, $R^{18}$ represents a hydrogen atom or a halogenated or non-halogenated alkyl group having a carbon number of from 1 to 5. $R^{19}$ represents a hydrogen atom or a hydroxyalkyl group. Also, j represents an integer of from 1 to 3.

Examples of the halogenated or non-halogenated alkyl group having a carbon number of from 1 to 5, which $R^{18}$ represents, include the same groups as those in the case of $R^{11}$. Of these, a methyl group, an ethyl group, and a trifluoromethyl group are preferable, with a methyl group and an ethyl group being more preferable.

The alkyl group in the hydroxyalkyl group which $R^{19}$ represents may be either linear or branched. A carbon number of the alkyl group is preferably from 1 to 5, and more preferably from 1 to 4. The alkyl group is still more preferably a methyl group, an n-propyl group, or an isopropyl group.

A hydroxyl group number in the hydroxyalkyl group of $R^{19}$ is preferably from 1 to 4, more preferably from 1 to 3, and still more preferably 1 or 2. The hydroxyl group is more preferably a primary hydroxyl group or a secondary hydroxyl group, and still more preferably a primary hydroxyl group.

In the present invention, $R^{19}$ is preferably a monohydroxyalkyl group, a dihydroxyalkyl group, or a hydrogen atom; and more preferably a monohydroxyethyl group, a monohydroxypropyl group, a dihydroxypropyl group, or a hydrogen atom.

j is preferably 1 or 2, and more preferably 1. In the case where j is 1, it is preferable that —OR$^{19}$ is bonded at the 3-position of the adamantyl group. In the case where j is 2, it is preferable that —OR$^{19}$ is bonded at the 3-position and 5-position of the adamantyl group.

As the constituent unit (a3'-1), it is preferable that j is 1; and it is especially preferable that —OR$^{19}$ is bonded at the 3-position of the adamantyl group. That is, as the constituent unit (a3'), a constituent unit represented by the following general formula (a3'-1-1) (in the following constituent unit, R$^{18}$ and R$^{19}$ are the same as defined above) is preferable.

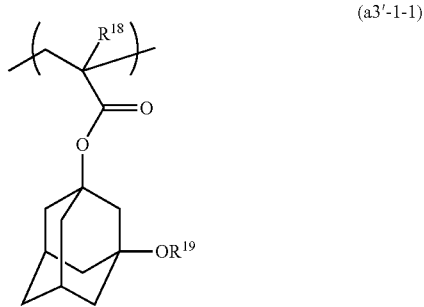

(a3'-1-1)

The constituent unit (a3") is a constituent unit which is derived from an acrylic acid not having a cyclic structure, namely an alicyclic hydrocarbon group or an aromatic hydrocarbon group, and having an alcoholic hydroxyl group in a side chain thereof.

Examples of the constituent unit having an alcoholic hydroxyl group in a side chain thereof include a hydroxyalkyl group-containing constituent unit.

In the hydroxyalkyl group, the alkyl group may be either linear or branched. A carbon number of the alkyl group is preferably from 1 to 20, more preferably from 1 to 16, and still more preferably from 1 to 12. A hydroxyl group number is preferably 1 or 2, and more preferably 1.

For example, the hydroxyalkyl group may be bonded directly to the carbon atom at the α-position of the main chain (the moiety in which the ethylenically double bond of acrylic acid is cleaved), or may be substituted with a hydrogen atom of the carboxyl group of acrylic acid to constitute an ester. In the constituent unit (a3"), it is preferable that the hydroxyalkyl group is present in at least one or both of them.

Incidentally, in the case where the hydroxyalkyl group is not bonded at the α-position, a halogenated or non-halogenated alkyl group may be bonded to the carbon atom at the α-position. With respect to the halogenated or non-halogenated alkyl group, there are exemplified the same groups as those in the case of R$^{11}$, and the same alkyl groups are preferable.

The constituent unit (a3") is preferably a constituent unit represented by the following general formula (a3"-1).

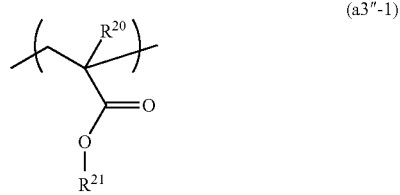

(a3"-1)

In the foregoing constituent unit, R$^{20}$ represents a hydrogen atom, a halogenated or non-halogenated alkyl group, or a hydroxyalkyl group; and R$^{21}$ represents an alkyl group or a hydroxyalkyl group, provided that at least one of R$^{20}$ and R$^{21}$ represents a hydroxyalkyl group.

The hydroxyalkyl group which R$^{20}$ represents is preferably a linear or branched hydroxyalkyl group having a carbon number of not more than 10, and more preferably a linear or branched hydroxyalkyl group having a carbon number of from 1 to 8. Though a hydroxyl group number in the hydroxyalkyl group is not particularly limited, it is in general 1. Also, the hydroxyl group is more preferably a primary or secondary hydroxyl group, and still more preferably a primary hydroxyl group. The hydroxyalkyl group which R$^{20}$ represents is yet still more preferably a hydroxymethyl group or a hydroxyethyl group.

A carbon number of the halogenated or non-halogenated alkyl group which R$^{20}$ represents is preferably not more than 10, more preferably from 1 to 8, and still more preferably 1 or 2. Examples of the halogenated or non-halogenated alkyl group which R$^{20}$ represents include a methyl group, a trifluoromethyl group, an ethyl group, a pentafluoroethyl group, various propyl groups, various butyl groups, and so on.

Examples of the alkyl group which R$^{21}$ represents include a methyl group, an ethyl group, various propyl groups, various butyl groups, various heptyl groups, various octyl groups, various decyl groups, various dodecyl groups, and so on. The alkyl group is preferably an alkyl group having a carbon number of not more than 10, more preferably an alkyl group having a carbon number of from 1 to 8, and still more preferably a methyl group or an ethyl group.

The hydroxyalkyl group which R$^{21}$ represents is preferably a linear or branched hydroxyalkyl group having a carbon number of not more than 10, more preferably a linear or branched hydroxyalkyl group having a carbon number of from 2 to 8, and still more preferably a hydroxyethyl group. Though a hydroxyl group number is not particularly limited, it is in general 1. Also, the hydroxyl group is more preferably a primary or secondary hydroxyl group, and still more preferably a primary hydroxyl group.

Also, in addition to the foregoing constituent units (a3') and (a3"), the following constituent unit (a3-2) is also preferably exemplified as the constituent unit (a3).

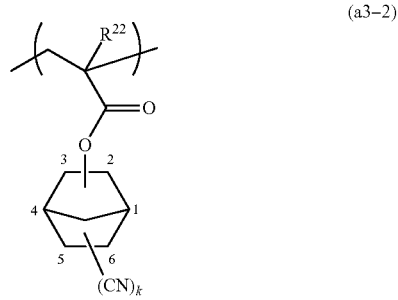

(a3-2)

In the foregoing constituent unit, R$^{22}$ represents a hydrogen atom or a halogenated or non-halogenated alkyl group having a carbon number of from 1 to 5; and k represents an integer of from 1 to 3.

Examples of the halogenated or non-halogenated alkyl group having a carbon number of from 1 to 5, which R$^{22}$ represents, include the same groups as those in the case of R$^{11}$.

k is preferably 1, and it is preferable that the cyano group is bonded at the 5-position or 6-position of the norbornyl group.

The foregoing constituent unit (a3) may be composed of only one kind, or may be composed of two or more kinds thereof.

In the case where the polymer has the constituent unit (a3), a proportion of the constituent unit (a3) is preferably from 5 to 50% by mole, more preferably from 5 to 40% by mole, and still more preferably from 5 to 25% by mole relative to the whole of the constituent units constituting the polymer of the present invention.

Also, in the case where the polymer has the constituent unit (a3), the constituent unit (a3) is preferably the constituent unit (a3'), more preferably a constituent unit of the constituent unit (a3'-1) wherein $R^{19}$ is a hydrogen atom, and still more preferably a constituent unit of the constituent unit (a3'-1-1) wherein $R^{19}$ is a hydrogen atom.

(Constituent Unit (a4))

The constituent unit (a4) is a constituent unit which is derived from a (meth)acrylic acid alicyclic hydrocarbon ester.

The constituent unit (a4) is effective for regulating the polarity of the polymer or regulating thermal physical properties of the polymer.

The alicyclic hydrocarbon group that is an alcohol residue of the (meth)acrylic acid alicyclic hydrocarbon ester may be monocyclic or polycyclic, and a carbon number forming the ring is preferably from 3 to 12, and more preferably from 6 to 12. From the viewpoint of easiness in industrial availability, the alicyclic hydrocarbon group is still more preferably a tricyclodecanyl group, an adamantyl group, a tetracyclododecanyl group, an isobornyl group, or a norbornyl group.

The alicyclic hydrocarbon group may have a substituent. The substituent is preferably a linear or branched alkyl group having a carbon number of from 1 to 5. Examples of the linear or branched alkyl group having a carbon number of from 1 to 5 include a methyl group, an ethyl group, various propyl groups, various butyl groups, and so on.

Specifically, the following constituent units are exemplified as the constituent unit (a4), but it should not be construed that the present invention is limited thereto.

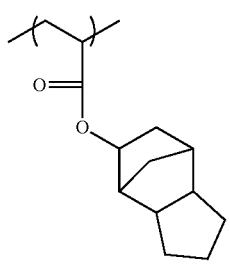
(a4-1)

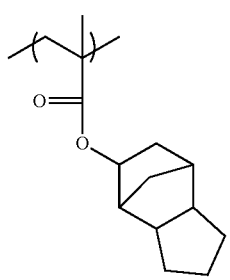
(a4-2)

-continued

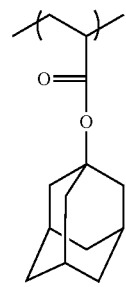
(a4-3)

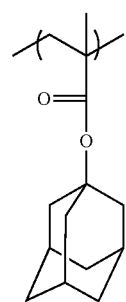
(a4-4)

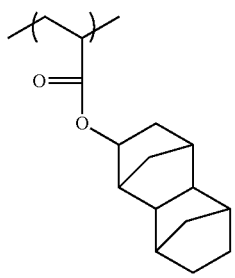
(a4-5)

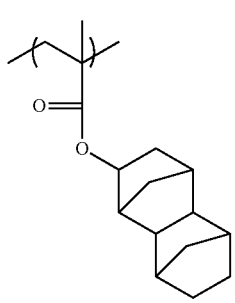
(a4-6)

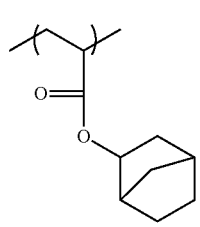
(a4-7)

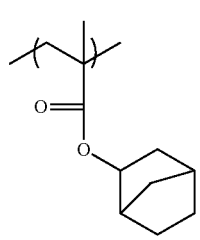
(a4-8)

(a4-9)
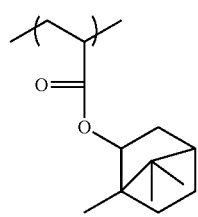
(a4-10)
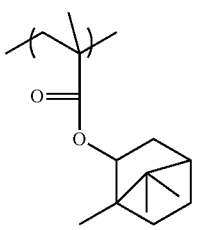
(a4-11)
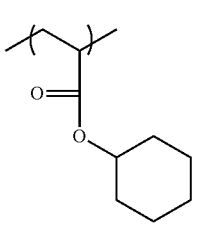
(a4-12)
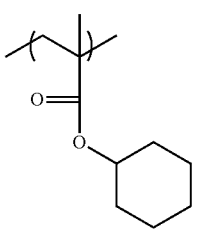
(a4-13)
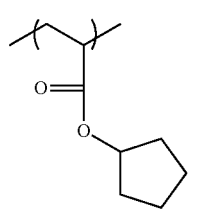
(a4-14)
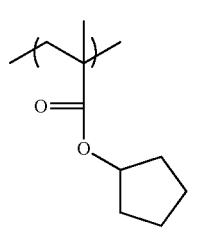
(a4-15)
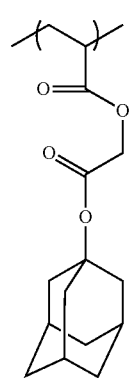
(a4-16)
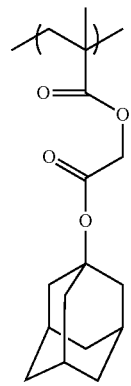
(a4-17)
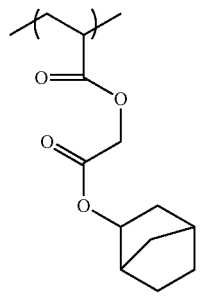
(a4-18)
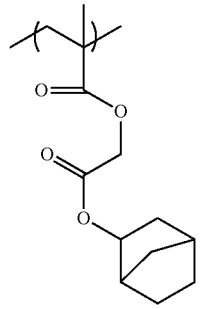

(a4-19)
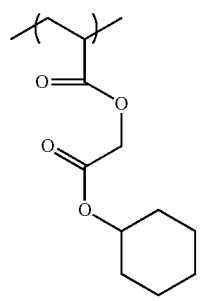

(a4-20)
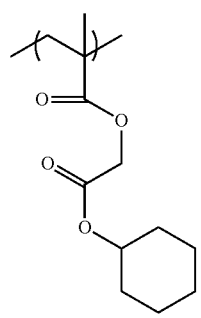

(a4-21)
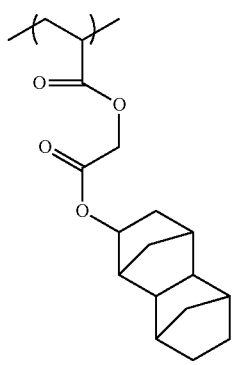

(a4-22)
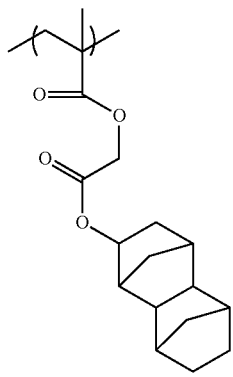

(a4-23)
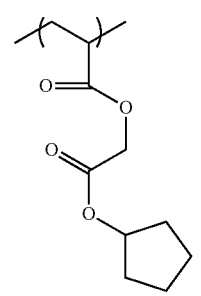

(a4-24)
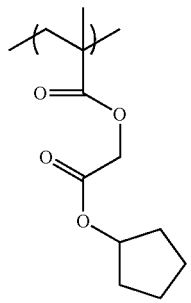

The foregoing constituent unit (a4) may be composed of only one kind, or may be composed of two or more kinds thereof.

In the case where the polymer has the constituent unit (a4), a proportion of the constituent unit (a4) is preferably from 1 to 30% by mole, and more preferably from 10 to 20% by mole relative to the whole of the constituent units constituting the polymer of the present invention.

(Constituent Unit (a5))

The constituent unit (a5) is other constituent unit which is not classified into the foregoing constituent units (1') and (a1) to (a4). As the constituent unit (a5), all of constituent units which have hitherto been known as a constituent unit of a polymer for photoresist for ArF excimer laser or KrF excimer laser (preferably for ArF excimer laser) or the like can be used. Specifically, the following constituent units are exemplified as the constituent unit (a5), but it should not be construed that the present invention is limited thereto.

(a5-1)
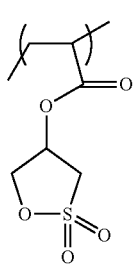

(a5-2)
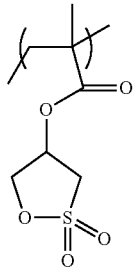

(a5-3)
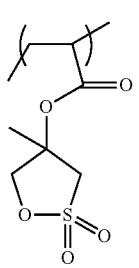

(a5-4)
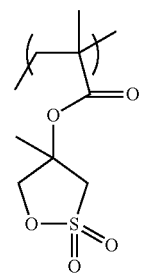
(a5-5)
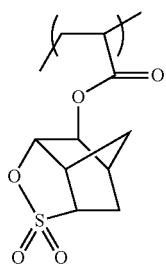
(a5-6)
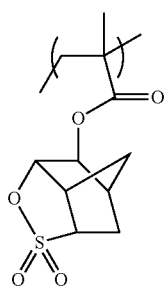
(a5-7)
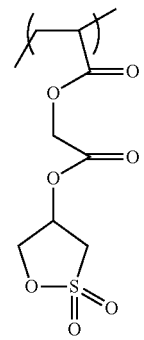
(a5-8)
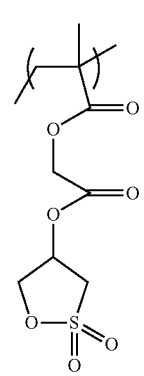
(a5-9)
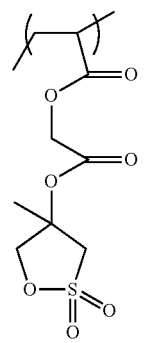
(a5-10)
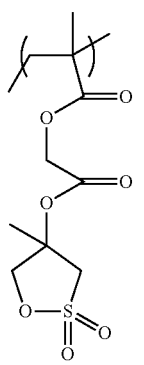
(a5-11)
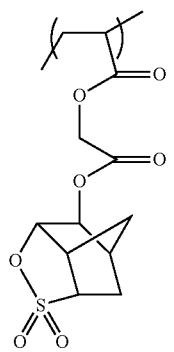
(a5-12)
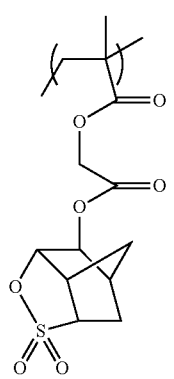

(a5-13)
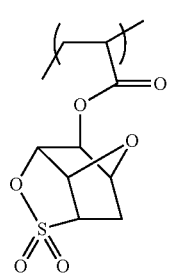

(a5-14)
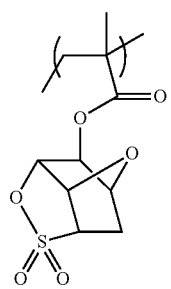

(a5-15)
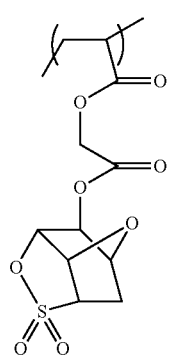

(a5-16)
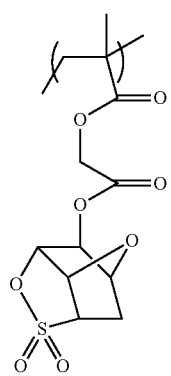

As described above, the polymer of the present invention may be a copolymer of the N-acyl-β-lactam derivative (1) and other polymerizable compound, namely a copolymer composed of the constituent unit (1') and other constituent unit.

As the preferred structure of the copolymer, there are exemplified the following copolymers (A1) to (A6) and so on.

Copolymer (A1): Copolymer having at least the constituent units (1') and (a1)

Copolymer (A2): Copolymer having at least the constituent units (1') and (a2)

Copolymer (A3): Copolymer having at least the constituent units (1') and (a3)

Copolymer (A4): Copolymer having at least the constituent units (1') and (a4)

Copolymer (A5): Copolymer having at least the constituent units (1'), (a1) and (a2)

Copolymer (A6): Copolymer having at least the constituent units (1'), (a1) and (a3)

(Manufacturing Method of Polymer)

The polymer can be manufactured by means of radical polymerization according to the usual way. In particular, as a method of synthesizing the polymer having a small molecular weight distribution, there can be exemplified living radical polymerization and so on. In a general radical polymerization method, one or more kinds of the N-acyl-β-lactam derivative (1) and if desired, one or more kinds of monomers corresponding to the foregoing constituent units (a1) to (a5) (hereinafter referred to as "copolymerization monomer") are polymerized in the presence of a radical polymerization initiator and solvent and if desired, a chain transfer agent.

A method of carrying out the radical polymerization is not particularly limited, and a customary method which is adopted in manufacturing, for example, an acrylic polymer, such as a solution polymerization method, an emulsion polymerization method, a suspension polymerization method, a bulk polymerization method, and the like, can be adopted.

Examples of the radical polymerization initiator which is used for the manufacture of the polymer of the present invention include a hydroperoxide compound such as t-butyl hydroperoxide, cumene hydroperoxide, and the like; a dialkyl peroxide compound such as di-t-butyl peroxide, t-butyl-α-cumyl peroxide, di-α-cumyl peroxide, and the like; a diacyl peroxide compound such as benzoyl peroxide, diisobutyryl peroxide, and the like; an azo compound such as 2,2'-azobisisobutyronitrile, dimethyl-2,2'-azobisisobutyrate, and the like; and so on.

Though a use amount of the radical polymerization initiator can be properly chosen depending upon kinds and use amounts of the N-acyl-β-lactam derivative (1), the copolymerization monomer, the chain transfer agent, and the solvent, each of which is used for the polymerization reaction; and a copolymerization condition such as a polymerization temperature and the like, it is in general from 0.005 to 0.2 mol, and preferably from 0.01 to 0.15 mol per 1 mol of the whole of the polymerizable compounds [referring to a total sum amount of the N-acyl-β-lactam derivative (1) and the copolymerization monomer; hereinafter the same].

Examples of the chain transfer agent which is used for the manufacture of the polymer of the present invention include a thiol compound such as dodecane thiol, mercapto ethanol, mercapto propanol, mercapto acetic acid, mercapto propionic acid, and the like. Such a thiol compound may be used alone or in admixture of two or more kinds thereof.

In the case of using the chain transfer agent, its use amount is in general from 0.005 to 0.2 mol, and preferably from 0.01 to 0.15 mol per 1 mol of the whole of the polymerizable compounds.

The manufacture of the polymer of the present invention is in general carried out in the presence of a solvent.

The solvent is not particularly limited so far as it does not inhibit the polymerization reaction. Examples thereof include a glycol ether such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, and the like; an ester such as ethyl lactate, methyl 3-methoxypropionate, methyl acetate, ethyl acetate, propyl acetate, and the like; a ketone such as acetone, methyl ethyl ketone, methyl isopropyl ketone, methyl isobutyl ketone, methyl amyl ketone, cyclopentanone, cyclohexanone, and the like; an ether such as diethyl ether, diisopropyl ether, dibutyl ether, tetrahydrofuran, 1,4-dioxane, and the like; and so on. Such a solvent may be used alone or in admixture of two or more kinds thereof.

A use amount of the solvent is in general from 0.5 to 20 parts by mass, and from the viewpoint of economy, preferably from 1 to 10 parts by mass, per part by mass of the whole of the polymerizable compounds.

In manufacturing the polymer of the present invention, a polymerization temperature is in general from 40 to 150° C., and from the viewpoint of stability of the produced polymer, preferably from 60 to 120° C.

A manufacturing time of the polymer of the present invention varies depending upon kinds and use amounts of the N-acyl-β-lactam derivative (1), the copolymerization monomer, the polymerization initiator, and the solvent; and a copolymerization condition such as a temperature of the polymerization reaction and the like, it is in general from 30 minutes to 48 hours, and more preferably from one hour to 24 hours.

The thus obtained polymer can be isolated by a usual operation such as reprecipitation and the like. The isolated polymer can also be dried by means of vacuum drying or the like.

Examples of a solvent which is used for the foregoing operation of reprecipitation include an aliphatic hydrocarbon such as pentane, hexane, and the like; an alicyclic hydrocarbon such as cyclohexane and the like; an aromatic hydrocarbon such as benzene, xylene, and the like; a halogenated hydrocarbon such as methylene chloride, chloroform, chlorobenzene, dichlorobenzene, and the like; a nitrated hydrocarbon such as nitromethane and the like; a nitrile such as acetonitrile, benzonitrile, and the like; an ether such as diethyl ether, diisopropyl ether, tetrahydrofuran, 1,4-dioxane, and the like; a ketone such as acetone, methyl ethyl ketone, and the like; a carboxylic acid such as acetic acid and the like; an ester such as ethyl acetate, butyl acetate, and the like; a carbonate such as dimethyl carbonate, diethyl carbonate, ethylene carbonate, and the like; an alcohol such as methanol, ethanol, propanol, isopropyl alcohol, butanol, and the like; and water. Such a solvent may be used alone or in admixture of two or more kinds thereof.

Though a use amount of the solvent varies depending upon the kind of the polymer and the kind of the solvent, in general, it is preferably from 0.5 to 100 parts by mass, and from the viewpoint of economy, more preferably from 1 to 50 parts by mass, per part by mass of the polymer.

(Weight Average Molecular Weight (Mw))

Though a weight average molecular weight (Mw) of the polymer is not particularly limited, when it is preferably from 500 to 50,000, and more preferably from 1,000 to 30,000, its usefulness as a component of a photoresist composition as described later is high. Such Mw is a value measured according to the method described in the Examples.

[Photoresist Composition]

The photoresist composition of the present invention contains a photo acid generator and a solvent and if desired, a basic compound, a surfactant, and other additives as described below, together with the foregoing polymer.

(Photo Acid Generator)

The photo acid generator is not particularly limited, and a known photo acid generator which has hitherto been generally used for a chemical amplification type resist can be used. Examples of the photo acid generator include an onium salt based photo acid generator such as an iodonium salt, a sulfonium salt, and the like; an oxysulfonate based photo acid generator; a bisalkyl or bisaryl sulfonyl diazomethane based photo acid generator; a nitrobenzyl sulfonate based photo acid generator; an imino sulfonate based photo acid generator; a disulfone based photo acid generator; and so on. Such a photo acid generator may be used alone or in admixture of two or more kinds thereof. Of these, an onium salt based photo acid generator is preferable. Furthermore, from the viewpoint of the fact that the intensity of the generated acid is strong, the following fluorine-containing onium salts containing a fluorine-containing alkylsulfonic acid ion as an anion are preferable.

Specific examples of the fluorine-containing onium salt include trifluoromethanesulfonate or nonafluorobutanesulfonate of diphenyliodonium; trifluoromethanesulfonate or nonafluorobutanesulfonate of bis(4-tert-butylphenyl)iodonium; trifluoromethanesulfonate, heptafluoropropanesulfonate or nonafluorobutanesulfonate of triphenylsulfonium; trifluoromethanesulfonate, heptafluoropropanesulfonate or nonafluorobutanesulfonate of tri(4-methylphenyl)sulfonium; trifluoromethanesulfonate, heptafluoropropanesulfonate or nonafluorobutanesulfonate of dimethyl(4-hydroxynaphthyl)sulfonium; trifluoromethanesulfonate, heptafluoropropanesulfonate or nonafluorobutanesulfonate of monophenyldimethylsulfonium; trifluoromethanesulfonate, heptafluoropropanesulfonate or nonafluorobutanesulfonate of diphenylmonomethylsulfonium; trifluoromethanesulfonate, heptafluoropropanesulfonate or nonafluorobutanesulfonate of (4-methylphenyl)diphenylsulfonium; trifluoromethanesulfonate, heptafluoropropanesulfonate or nonafluorobutanesulfonate of (4-methoxyphenyl)diphenylsulfonium; trifluoromethanesulfonate, heptafluoropropanesulfonate or nonafluorobutanesulfonate of tri(4-tert-butyl)phenylsulfonium; and so on. Such a fluorine-containing onium salt may be used alone or in admixture of two or more kinds thereof.

From the viewpoint of ensuring sensitivity and developability of the photoresist composition, in general, a blending amount of the photo acid generator is preferably from 0.1 to 30 parts by mass, and more preferably from 0.5 to 10 parts by mass based on 100 parts by mass of the polymer.

(Solvent)

Examples of the solvent which is blended in the photoresist composition include a glycol ether such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, and the like; an ester such as ethyl lactate, methyl 3-methoxypropionate, methyl acetate, ethyl acetate, propyl acetate, and the like; a ketone such as acetone, methyl ethyl ketone, methyl isopropyl ketone, methyl isobutyl ketone, methyl amyl ketone, cyclopentanone, cyclohexanone, and the like; an ether such as diethyl ether, diisopropyl ether, dibutyl ether, tetrahydrofuran, 1,4-dioxane, and the like; and so on. Such a solvent may be used alone or in admixture of two or more kinds thereof.

In general, a blending amount of the solvent is preferably from 1 to 50 parts by mass, and preferably from 2 to 25 parts by mass per part by mass of the polymer.

(Basic Compound)

For the purpose of enhancing the resolution while suppressing a diffusion rate of the acid in the photoresist film, if desired, a basic compound can be blended in an amount in the range where properties of the photoresist composition are not inhibited, in the photoresist composition. As such a basic compound, there can be exemplified an amide such as formamide, N-methylformamide, N,N-dimethylformamide, acetamide, N-methylacetamide, N,N-dimethylacetamide, N-(1- adamantyl)acetamide, benzamide, N-acetylethanolamine, 1-acetyl-3-methylpiperidine, pyrrolidone, N-methylpyrrolidone, s-caprolactam, δ-valerolactam, 2-pyrrolidinone, acrylamide, methacrylamide, t-butyl acrylamide, methylenebisacrylamide, methylenebismethacrylamide, N-methylolacrylamide, N-methoxyacrylamide, diacetoneacrylamide, and the like; and an amine such as pyridine, 2-methylpyridine, 4-methylpyridine, nicotine, quinoline, acridine, imidazole, 4-methylimidazole, benzimidazole, pyrazine, pyrazole, pyrrolidine, N-t-butoxycarbonylpyrrolidine, piperidine, tetrazole, morpholine, 4-methylmorpholine, piperazine, 1,4-diazabicyclo[2.2.2]octane, tributylamine, tripentylamine, trihexylamine, triheptylamine, trioctylamine, triethanolamine, and the like. Such a basic compound can be used alone or in admixture of two or more kinds thereof.

In the case of blending the basic compound, though its blending amount varies depending upon the kind of the used basic compound, in general, it is preferably from 0.01 to 10 mol, and more preferably from 0.05 to 1 mol per 1 mol of the photo acid generator.

(Surfactant)

For the purpose of enhancing the coatability, if desired, a surfactant can be blended in an amount in the range where properties of the photoresist composition is not inhibited, in the photoresist composition.

Examples of such a surfactant include polyoxyethylene lauryl ether, polyoxyethylene stearyl ether, polyoxyethylene oleyl ether, polyoxyethylene n-octylphenyl ether, and so on. Such a surfactant may be used alone or in admixture of two or more kinds thereof.

In the case of blending the surfactant, its blending amount is in general not more than 2 parts by mass based on 100 parts by mass of the polymer.

(Other Additives)

Furthermore, a sensitizer, a halation preventing agent, a shape improving agent, a storage stabilizer, a defoaming agent, and the like can be blended as other additives in an amount in the range where properties of the photoresist composition are not impaired, in the photoresist composition.

(Formation of Photoresist Pattern)

A prescribed resist pattern can be formed by coating the photoresist composition on a substrate, prebaking usually at from 70 to 160° C. for from 1 to 10 minutes, irradiating (exposing) radiations via a prescribed mask, then carrying out post-exposure baking at from 70 to 160° C. for 1 to 5 minutes to form a latent resist pattern, and subsequently developing with a developing solution.

For the exposure, radiations having various wavelengths, for example, ultraviolet rays, X-rays, and the like can be utilized. In general, excimer lasers such as g-rays, i-rays, XeCl, KrF, KrCl, ArF, ArCl, and the like are used for semiconductor resists. Of these, from the viewpoint of refinement, it is preferable to use an ArF excimer laser.

An exposure dose is preferably from 0.1 to 1,000 mJ/cm$^2$, and more preferably from 1 to 500 mJ/cm$^2$.

Examples of the developing solution include an alkaline aqueous solution in which an inorganic base such as sodium hydroxide, potassium hydroxide, sodium carbonate, ammonia water, and the like; an alkylamine such as ethylamine, diethylamine, triethylamine, and the like; an alcoholamine such as dimethylethanolamine, triethanolamine, and the like; a quaternary ammonium salt such as tetramethylammonium hydroxide, tetraethylammonium hydroxide, and the like; or the like is dissolved; and so on. Of these, it is preferable to use an alkaline aqueous solution in which a quaternary ammonium salt such as tetramethylammonium hydroxide, tetraethylammonium hydroxide, and the like is dissolved.

In general, a concentration of the developing solution is preferably from 0.1 to 20% by mass, and more preferably from 0.1 to 10% by mass.

EXAMPLES

The present invention is hereunder described in more detail with reference to the Examples, but it should be construed that the present invention is not limited thereto at all. Incidentally, a measurement method of Mw and Mn and a calculation method of a degree of dispersion in each of the Examples are as follows.

(Measurement of Mw and Mn and Calculation of Degree of Dispersion)

A weight average molecular weight (Mw) and a number average molecular weight (Mn) were determined as reduced values according to calibration curves prepared with standard polystyrene by carrying out gel permeation chromatography (GPC) measurement using a differential refractometer as a detector and using tetrahydrofuran (THF) as an eluent under the following condition. Also, a degree of dispersion (Mw/Mn) was determined by dividing the weight average molecular weight (Mw) by the number average molecular weight (Mn).

GPC measurement: A column obtained by connecting three of "TSK-gel supermultipore HZ-M" (a trade name, manufactured by Tosoh Corporation, 4.6 mm×150 mm) to each other in series was used, and the measurement was carried out under a condition at a column temperature of 40° C., a differential refractometer temperature of 40° C. and a flow rate of the eluent of 0.35 mL/min.

Also, the measurement of a film dissolution minimum exposure dose of the photoresist composition obtained in each of the Examples was carried out in the following manner.

(Measurement of Film Dissolution Minimum Exposure Dose)

The photoresist composition obtained in each of the Examples was coated on a silicon wafer having a diameter of 10 cm by a spin coating method and prebaked on a hot plate at 130° C. for 90 seconds, thereby forming a resist film having a film thickness of 100 nm.

An ArF excimer laser having a wavelength of 193 nm was exposed on the obtained resist film through a slit of 1 mm×5 mm, while changing stepwise the exposure dose. After the exposure, post-exposure baking was carried out on a hot plate at a temperature shown in FIG. 1 for 90 seconds, and thereafter, the resultant was developed with a 2.38% by mass tetramethylammonium hydroxide aqueous solution for 90 seconds.

The wafer after the development was visually observed, thereby determining a minimum exposure dose at which the resist caused film dissolution (an exposure dose at which 80% or more of an exposed area was dissolved was defined as a minimum exposure dose).

Synthesis Example 1

Synthesis of 6-azabicyclo[3.2.0]heptan-7-one

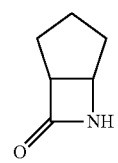

In a four-necked flask with a volume of 1 L, which was equipped with a dropping funnel, a thermometer, and a nitrogen introducing tube, 150 g (2.2 mol) of cyclopentene and 450 g of toluene were charged, and 311 g (2.2 mol) of chlorosulfonyl isocyanate was added dropwise at 20° C. After completion of the dropwise addition, the mixture was further stirred at 30° C. for 48 hours.

The obtained reaction mixture was added dropwise to 1,300 g of a 20% sodium sulfite aqueous solution and hydrolyzed, and thereafter, the resultant was separated into an organic layer and an aqueous layer. The aqueous layer was extracted twice with 1,000 g of ethyl acetate. The organic layer and the extract were mixed and concentrated under reduced pressure, thereby obtaining 210 g (1.9 mol) of 6-azabicyclo[3.2.0]heptan-7-one having the following properties.

$^1$H-NMR (300 MHz, CDCl$_3$, ppm, TMS) δ: 1.32-2.09 (6H, m, CH$_2$×3), 3.49-3.54 (1H, m, CH), 4.04-4.08 (1H, m, CH), 5.52 (1H, bs, NH)

Example 1

Synthesis of 6-methacryloyl-6-azabicyclo[3.2.0]heptan-7-one

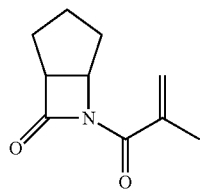

In a three-necked flask with a volume of 50 mL, which was equipped with a dropping funnel, a thermometer, and a nitrogen introducing tube, 2 g (18 mmol) of 6-azabicyclo[3.2.0]heptan-7-one obtained in Synthesis Example 1, 2.7 g (27 mmol) of triethylamine, 0.22 g (1.8 mmol) of 4-(N,N-dimethylamino)pyridine, and 6 g of methylene chloride were charged. To this mixed solution, 2.3 g (20 mmol) of methacryloyl chloride was added at 20° C., and the mixture was stirred at room temperature for 2 hours.

7 g of water was added dropwise to the obtained reaction mixture, thereby separating it into an organic layer and an aqueous layer. The aqueous layer was extracted twice with 7 g of methylene chloride. The organic layer and the extract were mixed and concentrated under reduced pressure. The concentrate was purified by means of silica gel column chromatography, thereby obtaining 2.6 g (14.4 mmol) of 6-methacryloyl-6-azabicyclo[3.2.0]heptan-7-one having the following properties.

$^1$H-NMR (300 MHz, CDCl$_3$, ppm, TMS) δ: 1.48-2.35 (6H, m, CH$_2$×3), 2.00 (3H, s, CH$_3$), 3.53 (1H, m, CH), 4.50 (1H, m, CH), 5.75 (1H, m, CH$_2$), 6.00 (1H, s, CH$_2$)

Synthesis Example 2

Synthesis of 9-azatetracyclo[5.4.1.0$^{2.6}$.0$^{8.11}$]undecan-10-one

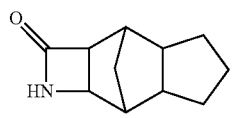

In a four-necked flask with a volume of 1 L, which was equipped with a dropping funnel, a thermometer, and a nitrogen introducing tube, 2.9 g (22 mmol) of dicyclopentadiene and 5 g of toluene were charged, and 3.1 g (22 mmol) of chlorosulfonyl isocyanate was added dropwise at 20° C. After completion of the dropwise addition, the mixture was further stirred at 30° C. for 16 hours. The obtained reaction mixture was added dropwise to 13 g of a 20% sodium sulfite aqueous solution and hydrolyzed, and thereafter, the resultant was separated into an organic layer and an aqueous layer. The aqueous layer was extracted twice with 10 g of toluene. The organic layer and the extract were mixed to obtain a reaction intermediate-containing toluene solution. The toluene solution was transferred into an autoclave having a volume of 200 mL, to which was then added 0.2 g of 10% by mass-palladium carbon, and the mixture was then stirred under a condition at an internal temperature of 60° C. and a hydrogen pressure of 0.5 MPa for 6 hours. After the internal temperature was cooled to 25° C., the palladium carbon was filtered off, and the filtrate was concentrated under reduced pressure, thereby obtaining 3.2 g (18 mmol) of 9-azatetracyclo[5.4.1.0$^{2.6}$.0$^{8.11}$]undecan-10-one having the following properties.

$^1$H-NMR (400 MHz, CDCl$_3$, ppm, TMS) δ: 1.42-1.66 (7H, m), 1.79 (1H, d, J=10.8 Hz), 2.35 (2H, d, J=4.0 Hz), 2.43-2.48 (1H, m), 2.54-2.57 (1H, m), 3.24 (1H, dd, J=3.2, 1.6 Hz), 3.62 (1H, d, J=3.6 Hz), 5.79 (1H, br)

Example 2

Synthesis of 9-methacryloyl-9-azatetracyclo[5.4.1.0$^{2.6}$.0$^{8.11}$]undecan-10-one

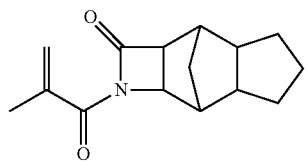 [SMILES: C=C(C)C(=O)N1C(=O)C2C3CC(C4CCCC43)C21]

The same procedure as those in Example 1 were followed, except for using 3.2 g (18 mmol) of 9-azatetracyclo[5.4.1.0$^{2.6}$.0$^{8.11}$]undecan-10-one obtained in Synthesis Example 2 in place of 6-azabicyclo[3.2.0]heptan-7-one, thereby obtaining 3.2 g (13 mmol) of 9-methacryloyl-9-azatetracyclo[5.4.1.0$^{2.6}$.0$^{8.11}$]undecan-10-one having the following properties.

$^1$H-NMR (400 MHz, CDCl$_3$, ppm, TMS) δ: 1.42-1.57 (5H, m), 1.63-1.70 (3H, m), 1.98 (3H, s), 2.46 (1H, d, J=4.4 Hz), 2.52 (1H, m), 2.59 (1H, m), 2.79 (1H, d, J=4.4 Hz), 3.23 (1H, d, J=4.4 Hz), 4.10 (1H, d, J=4.4 Hz), 5.72 (1H, m), 5.98 (1H, s)

Synthesis Example 3

Synthesis of 6-chloroacetyl-6-azabicyclo[3.2.0]heptan-7-one

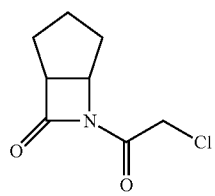 [SMILES: O=C(CCl)N1C(=O)C2CCCC21]

In a four-necked flask with a volume of 300 mL, which was equipped with a thermometer, a stirrer, a dropping funnel, and a nitrogen introducing tube, 11.1 g (100 mmol) of 6-azabicyclo[3.2.0]heptan-7-one, 100 mL of tetrahydrofuran, and 12.1 g (120 mmol) of triethylamine were charged, and an internal temperature was cooled to 3° C. 12.4 g (110 mmol) of 2-chloroacetyl chloride was added dropwise at that temperature over 15 minutes from the dropping funnel. After completion of the dropwise addition, the mixture was stirred for 3 hours. Thereafter, 50 mL of water and 50 mL of ethyl acetate were added, and a liquid separation operation was carried out. The obtained organic layer was concentrated under reduced pressure, thereby obtaining 8.4 g (45 mmol) of 6-chloroacetyl-6-azabicyclo[3.2.0]heptan-7-one having the following properties.

$^1$H-NMR (400 MHz, CDCl$_3$, ppm, TMS) δ: 1.46-1.68 (3H, m), 1.89-2.00 (1H, m), 2.10-2.19 (1H, m), 2.33 (1H, dd, J=14.2, 5.8 Hz), 3.60 (1H, dd, J=8.2, 4.6 Hz), 4.38 (1H, s), 4.40 (1H, s), 4.49 (1H, t, J=4.8 Hz)

Example 3

Synthesis of 6-methacryloyloxyacetyl-6-azabicyclo[3.2.0]heptan-7-one

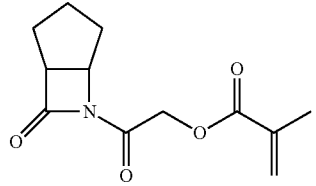 [SMILES: C=C(C)C(=O)OCC(=O)N1C(=O)C2CCCC21]

In a four-necked flask with a volume of 500 mL, which was equipped with a thermometer, a stirrer, a dropping funnel, and a nitrogen introducing tube, 9.7 g (70 mmol) of potassium carbonate, 0.7 g (4 mmol) of potassium iodide, 100 mL of dimethylformamide, 25.8 g (300 mmol) of methacrylic acid, and 18.8 g (100 mmol) of 6-chloroacetyl-6-azabicyclo[3.2.0]heptan-7-one obtained in Synthesis Example 3 were charged, and the mixture was stirred at an internal temperature of 25° C. for 5 hours. To the reaction mixture, 100 mL of ethyl acetate and 50 mL of water were added, and a liquid separation operation was then carried out. The obtained organic layer was concentrated under reduced pressure and then purified by means of silica gel column chromatography, thereby obtaining 17.1 g (72 mmol) of 6-methacryloyloxyacetyl-6-azabicyclo[3.2.0]heptan-7-one having the following properties.

$^1$H-NMR (400 MHz, CDCl$_3$, ppm, TMS) δ: 1.48-1.67 (3H, m), 1.93 (1H, t, J=6.4 Hz), 1.99 (3H, s), 2.12 (1H, dd, J=12.4, 4.6 Hz), 2.33 (1H, dd, J=14.2, 5.4 Hz), 3.59 (1H, dd, J=8.0, 4.4 Hz), 4.46 (1H, t, J=4.6 Hz), 5.00 (2H, s), 5.66 (1H, m), 6.22 (1H, m)

Synthesis Example 4

Synthesis of spiro[azetidin-2-one-2,2'-3',3'-dimethylbicyclo[2.2.1]heptane]

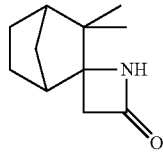

In a four-necked flask with a volume of 1 L, which was equipped with a dropping funnel, a thermometer, and a nitrogen introducing tube, 299.7 g (2.2 mol) of camphene and 450 g of toluene were charged, and 311 g (2.2 mol) of chlorosulfonyl isocyanate was added dropwise at 20° C. After completion of the dropwise addition, the mixture was further stirred at 30° C. for 48 hours.

The obtained reaction mixture was added dropwise to 1,300 g of a 20% sodium sulfite aqueous solution and hydrolyzed, and thereafter, the resultant was separated into an organic layer and an aqueous layer. The aqueous layer was extracted twice with 1,000 g of ethyl acetate. The organic layer and the extract were mixed and concentrated under reduced pressure, thereby obtaining 304.7 g (1.7 mol) of spiro[azetidin-2-one-2,2'-3',3'-dimethylbicyclo[2.2.1]heptane] having the following properties.

$^1$H-NMR (400 MHz, CDCl$_3$, ppm, TMS) δ: 0.91 (3H, s), 1.00 (3H, s), 1.20-1.33 (2H, m), 1.63 (1H, dd, J=12.2, 8.4 Hz), 1.82-1.88 (3H, m), 1.94-1.99 (1H, m), 2.10 (1H, d, J=17.2 Hz), 2.25 (1H, d, J=17.2 Hz), 3.49 (1H, dd, J=8.2, 4.6 Hz), 6.4 (1H, br)

Example 4

Synthesis of spiro[1-methacryloylazetidin-2-one-2,2'-3',3'-dimethylbicyclo[2.2.1]heptane]

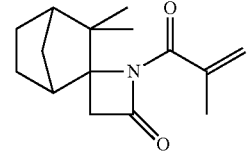 [SMILES: C=C(C)C(=O)N1C(=O)CC12C1CCC(C1)C2(C)C]

In a three-necked flask with a volume of 50 mL, which was equipped with a dropping funnel, a thermometer, and a nitrogen introducing tube, 3.2 g (18 mmol) of spiro[azetidin-2-one-2,2'-3',3'-dimethylbicyclo[2.2.1]heptane] obtained in Synthesis Example 4, 2.7 g (27 mmol) of triethylamine, 0.22 g (1.8 mmol) of 4-(N,N-dimethylamino)pyridine, and 6 g of methylene chloride were charged. To this mixed solution, 2.3 g (20 mmol) of methacryloyl chloride was added at 20° C., and the mixture was stirred at room temperature for 2 hours.

7 g of water was added dropwise to the obtained reaction mixture, thereby separating it into an organic layer and an aqueous layer. The aqueous layer was extracted twice with 7 g of methylene chloride. The organic layer and the extract were mixed and concentrated under reduced pressure. The concentrate was purified by means of silica gel column chromatography, thereby obtaining 3.3 g (13.7 mmol) of spiro[1-methacryloylazetidin-2-one-2,2'-3',3'-dimethylbicyclo[2.2.1]heptane] having the following properties.

$^1$H-NMR (400 MHz, CDCl$_3$, ppm, TMS) δ: 0.95 (3H, s), 0.99 (3H, s), 1.30-1.37 (2H, m), 1.85-1.92 (3H, m), 1.94-1.98 (2H, m), 1.97 (3H, s), 2.37 (1H, d, J=18.4 Hz), 2.46 (1H, d, J=18.4 Hz), 3.89 (1H, dd, J=7.4, 5.4 Hz), 5.35 (1H, s), 5.39 (1H, s)

Synthesis Example 5

Synthesis of 3-acetoxyazetidinone

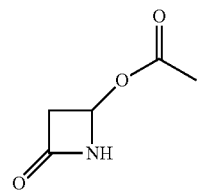

In a four-necked flask with a volume of 1 L, which was equipped with a dropping funnel, a thermometer, and a nitrogen introducing tube, 189.4 g (2.2 mol) of vinyl acetate was charged, and 56.6 g (0.4 mol) of chlorosulfonyl isocyanate was added dropwise at 3° C. After completion of the dropwise addition, the mixture was further stirred at 3° C. for 48 hours.

The obtained reaction mixture was added dropwise to 174 g of sodium sulfite, 93 g of sodium hydrogencarbonate, and 1,500 g of water and hydrolyzed. The resultant was extracted three times with 500 g of chloroform. The organic layer was concentrated under reduced pressure, thereby obtaining 127.8 g (1.0 mol) of 3-acetoxyazetidinone having the following properties.

$^1$H-NMR (400 MHz, CDCl$_3$, ppm, TMS) δ: 2.11 (3H, s), 2.99 (1H, dd, J=15.4, 1.2 Hz), 3.27 (1H, dd, J=15.4, 4.0 Hz), 5.84 (1H, dd, J=4.0, 1.2 Hz), 7.20 (1H, br)

Example 5

Synthesis of N-methacryloyl-3-acetoxyazetidinone

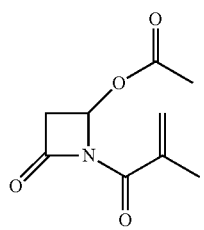

In a three-necked flask with a volume of 50 mL, which was equipped with a dropping funnel, a thermometer, and a nitrogen introducing tube, 2.3 g (18 mmol) of 3-acetoxyazetidinone obtained in Synthesis Example 5, 2.7 g (27 mmol) of triethylamine, 0.22 g (1.8 mmol) of 4-(N,N-dimethylamino) pyridine, and 6 g of methylene chloride were charged. To this mixed solution, 2.3 g (20 mmol) of methacryloyl chloride was added at 20° C., and the mixture was stirred at room temperature for 2 hours.

7 g of water was added dropwise to the obtained reaction mixture, thereby separating it into an organic layer and an aqueous layer. The aqueous layer was extracted twice with 7 g of methylene chloride. The organic layer and the extract were mixed and concentrated under reduced pressure. The concentrate was purified by means of silica gel column chromatography, thereby obtaining 2.6 g (13.3 mmol) of N-methacryloyl-3-acetoxyazetidinone having the following properties.

$^1$H-NMR (400 MHz, CDCl$_3$, ppm, TMS) δ: 2.00 (3H, s), 2.11 (3H, s), 2.99 (1H, dd, J=15.4, 1.2 Hz), 3.77 (1H, dd, J=15.4, 4.0 Hz), 5.84 (1H, dd, J=4.0, 1.2 Hz), 5.75 (1H, m), 6.00 (1H, s)

Example 6

Synthesis of Polymer (A)

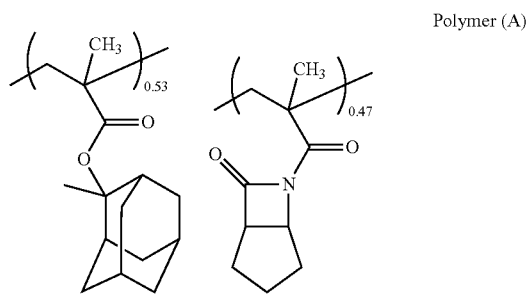

In a three-necked flask with an inner volume of 50 mL, which was equipped with a magnetic stirrer, a reflux condenser, and a thermometer, 5.51 g (23 mmol) of 2-methacryloyloxy-2-methyladamantane, 3.58 g (20 mmol) of 6-methacryloyl-6-azabicyclo[3.2.0]heptan-7-one obtained in Example 1, and 36.4 g of methyl ethyl ketone were charged, and nitrogen bubbling was carried out for 10 minutes. 0.36 g (2 mmol) of 2,2'-azobisisobutyronitrile was charged under a nitrogen atmosphere, and the mixture was subjected to a polymerization reaction at 80° C. for 4 hours.

The obtained reaction mixture was added dropwise to 220 g of methanol at room temperature while stirring, and a formed precipitate was collected by filtration. The precipitate was dried under reduced pressure (26.7 Pa) at 50° C. for 5 hours, thereby obtaining 7.3 g of Polymer (A) composed of the foregoing repeating units (the numerical values express a molar ratio). The obtained Polymer (A) had a weight average molecular weight (Mw) of 8,000 and a degree of dispersion of 2.0.

Example 7

Synthesis of Polymer (B)

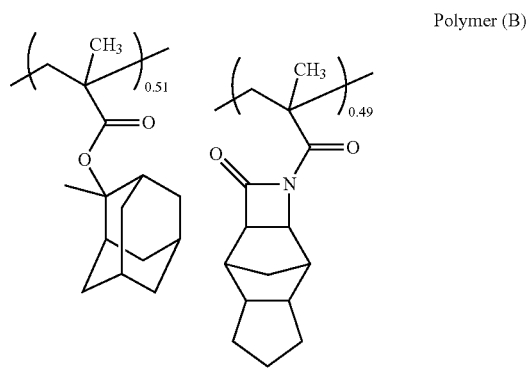

The same procedure as those in Example 6 were followed, except for using 4.9 g (20 mmol) of 9-methacryloyl-9-azatetracyclo[5.4.1.0$^{2.6}$.0$^{8.11}$]undecan-10-one obtained in Example 2 in place of 3.58 g (20 mmol) of 6-methacryloyl-6-azabicyclo[3.2.0]heptan-7-one, thereby obtaining 7.2 g of Polymer (B) composed of the foregoing repeating units (the numerical values express a molar ratio). The obtained Polymer (B) had an Mw of 8,500 and a degree of dispersion of 1.8.

Example 8

Synthesis of Polymer (C)

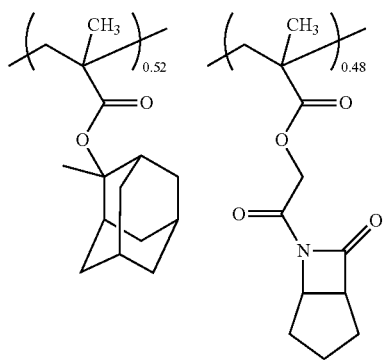

Polymer (C)

The same procedure as those in Example 6 were followed, except for using 4.7 g (20 mmol) of 6-methacryloyloxy-acetyl-6-azabicyclo[3.2.0]heptan-7-one obtained in Example 3 in place of 3.6 g (20 mmol) of 6-methacryloyl-6-azabicyclo[3.2.0]heptan-7-one, thereby obtaining 6.8 g of Polymer (C) composed of the foregoing repeating units (the numerical values express a molar ratio). The obtained Polymer (C) had an Mw of 9,200 and a degree of dispersion of 1.7.

Example 9

Synthesis of Polymer (D)

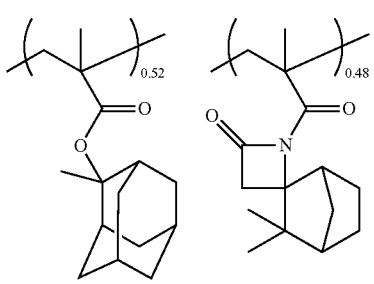

Polymer (D)

The same procedure as those in Example 6 were followed, except for using 4.95 g (20 mmol) of spiro[1-methacryloyl-azetidin-2-one-2,2'-3',3'-dimethylbicyclo[2.2.1]heptane] obtained in Example 4 in place of 3.6 g (20 mmol) of 6-methacryloyl-6-azabicyclo[3.2.0]heptan-7-one, thereby obtaining 6.8 g of Polymer (D) composed of the foregoing repeating units (the numerical values express a molar ratio). The obtained Polymer (D) had a weight average molecular weight (Mw) of 8,500 and a degree of dispersion of 2.0.

Example 10

Synthesis of Polymer (E)

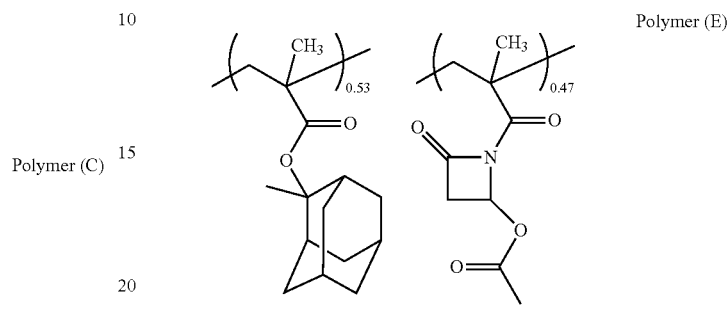

Polymer (E)

The same procedure as those in Example 6 were followed, except for using 3.9 g (20 mmol) of N-methacryloyl-3-acetoxyazetidinone obtained in Example 5 in place of 3.6 g (20 mmol) of 6-methacryloyl-6-azabicyclo[3.2.0]heptan-7-one, thereby obtaining 5.4 g of Polymer (E) composed of the foregoing repeating units (the numerical values express a molar ratio). The obtained Polymer (E) had a weight average molecular weight (Mw) of 9,800 and a degree of dispersion of 1.9.

Referential Example 1

Synthesis of Polymer (F)

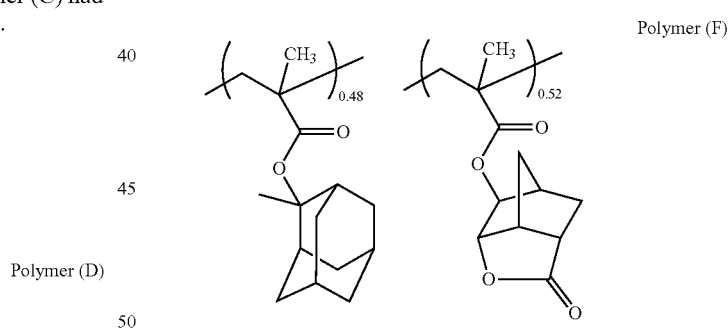

Polymer (F)

The same procedure as those in Example 6 were followed, except for using 5.11 g (23 mmol) of 5-methacryloyloxy-2,6-norbornane carbolactone in place of 3.58 g (20 mmol) of 6-methacryloyl-6-azabicyclo[3.2.0]heptan-7-one, thereby obtaining 6.3 g of Polymer (F) composed of the foregoing repeating units (the numerical values express a molar ratio). The obtained Polymer (F) had an Mw of 11,800 and a degree of dispersion of 1.7.

Example 11

Photoresist Composition A 100 parts by mass of Polymer (A) obtained in Example 6, 4.5 parts by mass of TPS-09 (a trade name, manufactured by Midori Kagaku Co., Ltd., component: triphenylsulfonium nonafluoro-n-butanesulfonate) as a photo acid generator, and 1,896 parts by mass of a propylene glycol monomethyl ether acetate/cyclohexanone mixed solvent (mass ratio: 1/1) as a solvent were mixed to obtain a solution in which the respective components were uniform. Thereafter, the obtained solution was filtered with a membrane filter having a pore size of 0.2 thereby obtaining Photoresist Composition A (total solid content concentration: about 5% by mass).

By using the obtained Photoresist Composition A, a film dissolution minimum exposure dose was measured according to the foregoing method. The results are shown in FIG. 1.

Example 12

Photoresist Composition B

The same procedure as those in Example 11 were followed, except for using 100 parts by mass of Polymer (B) obtained in Example 7 in place of 100 parts by mass of the Polymer (A), thereby obtaining Photoresist Composition B. By using the obtained Photoresist Composition B, a film dissolution minimum exposure dose was measured according to the foregoing method. The results are shown in FIG. 1.

Example 13

Photoresist Composition C

The same procedure as those in Example 11 were followed, except for using 100 parts by mass of Polymer (C) obtained in Example 8 in place of 100 parts by mass of the Polymer (A), thereby obtaining Photoresist Composition C. By using the obtained Photoresist Composition C, a film dissolution minimum exposure dose was measured according to the foregoing method. The results are shown in FIG. 1.

Example 14

Photoresist Composition D

Figure 2:
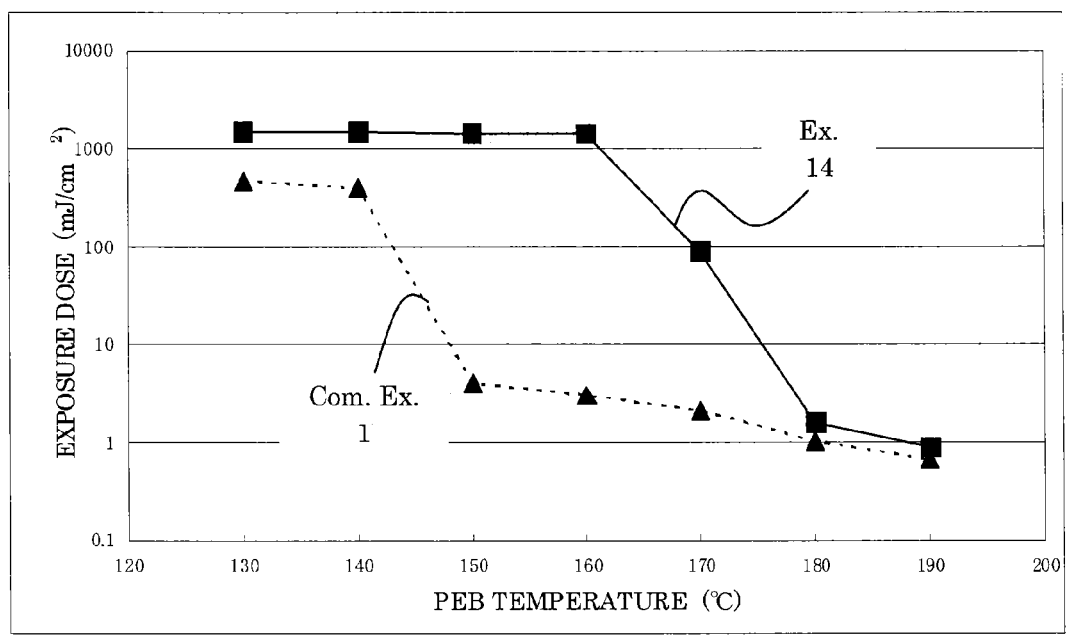
FIG. 2 is a graph showing a correlation between a post-exposure bake (PEB) temperature of a photoresist film formed from Photoresist Composition D obtained in Example 14 and Photoresist Composition F obtained in Comparative Example 1 and an exposure dose of light irradiated until the photoresist film has caused film dissolution.

The same procedure as those in Example 11 were followed, except for using 100 parts by mass of Polymer (D) obtained in Example 9 in place of 100 parts by mass of the Polymer (A), thereby obtaining Photoresist Composition D. By using the obtained Photoresist Composition D, a film dissolution minimum exposure dose was measured according to the foregoing method. The results are shown in FIG. 2.

Example 15

Photoresist Composition E

Figure 3:
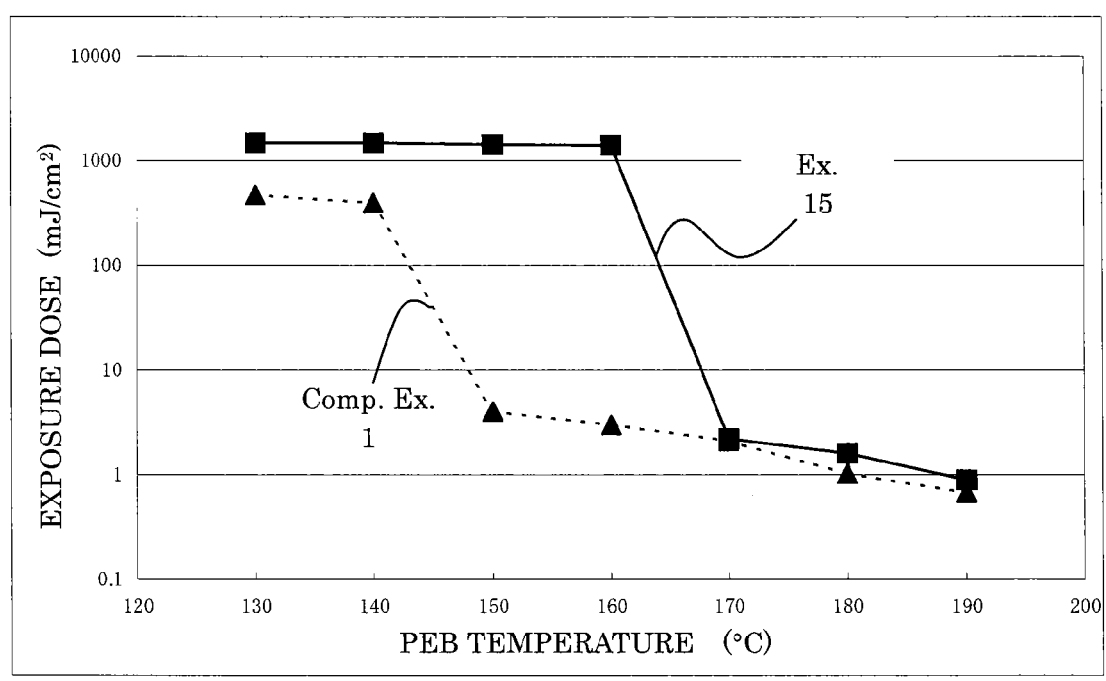
FIG. 3 is a graph showing a correlation between a post-exposure bake (PEB) temperature of a photoresist film formed from Photoresist Composition E obtained in Example 15 and Photoresist Composition F obtained in Comparative Example 1 and an exposure dose of light irradiated until the photoresist film has caused film dissolution.

The same procedure as those in Example 11 were followed, except for using 100 parts by mass of Polymer (E) obtained in Example 10 in place of 100 parts by mass of the Polymer (A), thereby obtaining Photoresist Composition E. By using the obtained Photoresist Composition E, a film dissolution minimum exposure dose was measured according to the foregoing method. The results are shown in FIG. 3.

Comparative Example 1

Photoresist Composition F

The same procedure as those in Example 11 were followed, except for using Polymer (F) in place of the Polymer (A), thereby obtaining Photoresist Composition F. By using the obtained Photoresist Composition F, a film dissolution minimum exposure dose was measured according to the foregoing method. The results are shown in FIGS. 1 to 3, respectively.

It is noted from FIGS. 1 to 3 that as compared with Photoresist Composition F, Photoresist Compositions A to E of the present invention each containing a polymer obtained using the N-acyl-β-lactam derivative (1) are very high in the post-exposure bake temperature at which the film dissolution exposure dose is lowered. Incidentally, it may be said from FIG. 1 that among Photoresist Compositions A to C, the acid diffusion length becomes short in the order of C>A>B.

In Photoresist Compositions A to E, the structural unit which is derived from an acid dissociable dissolution inhibiting group-containing acrylic ester is common, and a generated acid dissociation reaction is the same; and therefore, it may be said that when the photoresist composition of the present invention containing a polymer having the constituent unit (1') is used, the acid diffusion length becomes short characteristically. When the acid diffusion length becomes short, LWR can be improved; and therefore, it is noted that when the photoresist composition of the present invention is used, a resist pattern having a high resolution is formed.

INDUSTRIAL APPLICABILITY

The photoresist composition of the present invention is useful for the manufacture of semiconductors or printed wiring boards because LWR is improved, and a resist pattern having a high resolution is formed.

The invention claimed is:

1. An N-acyl-β-lactam derivative represented by formula (1):

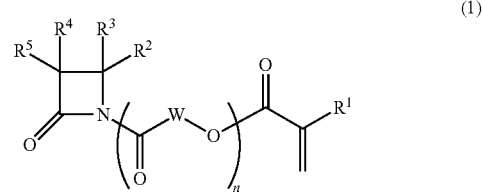

wherein
R$^1$ represents a hydrogen atom, a methyl group, or a trifluoromethyl group;
W represents an alkylene group having a carbon number of from 1 to 10 or a cycloalkylene group having a carbon number of from 4 to 10;
n represents 1; and
each of R$^2$, R$^3$, R$^4$, and R$^5$ independently represents a hydrogen atom, an alkyl group having a carbon number of from 1 to 5, a cyclic hydrocarbon group having a carbon number of from 3 to 10, or an acyloxy group having a carbon number of from 2 to 6,
provided that R$^3$ and R$^4$ are connected to each other to form a substituted or unsubstituted ring 2) having a ring forming atom number of from 4 to 10, said ring 2) optionally comprising an oxygen atom.

2. The N-acyl-β-lactam derivative of claim 1, wherein the R$^3$ and R$^4$ are connected to each other to form a substituted or unsubstituted ring 2) having a ring forming atom number of 10, said ring 2) optionally comprising an oxygen atom.

3. The N-acyl-β-lactam derivative claim 1, which is represented by the formula (1-1):

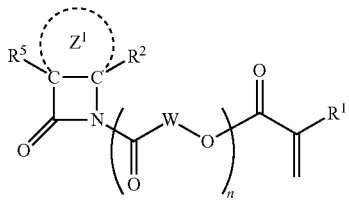

(1-1)

wherein

R$^1$ represents a hydrogen atom, a methyl group, or a trifluoromethyl group;

each of R$^2$ and R$^5$ independently represents a hydrogen atom or an alkyl group having a carbon number of from 1 to 5;

W represents an alkylene group having a carbon number of from 1 to 10 or a cycloalkylene group having a carbon number of from 4 to 10;

n represents 1; and

Z$^1$ represents a ring formed together with the two carbon atoms on the β-lactam, with a number of atoms forming the ring being from 3 to 10.

4. The N-acyl-β-lactam derivative of claim 3, wherein Z$^1$ represents a ring formed together with the two carbon atoms on the β-lactam, with a number of atoms forming the ring being 10.

5. A polymer obtained by polymerizing the N-acyl-β-lactam derivative represented by formula (1) or (1-1):

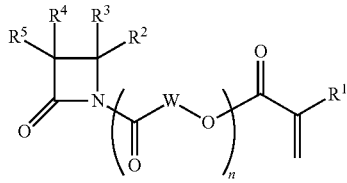

(1)

wherein:

R$^1$ represents a hydrogen atom, a methyl group, or a trifluoromethyl group;

W represents an alkylene group having a carbon number of from 1 to 10 or a cycloalkylene group having a carbon number of from 4 to 10;

n represents 0 or 1; and each of R$^2$, R$^3$, R$^4$, and R$^5$ independently represents a hydrogen atom, an alkyl group having a carbon number of from 1 to 5, a cyclic hydrocarbon group having a carbon number of from 3 to 10, or an acyloxy group having a carbon number of from 2 to 6, provided that R$^3$ and R$^4$ are connected to each other to form a substituted or unsubstituted ring 2) having a ring forming atom number of from 4 to 10, said ring 2) optionally comprising an oxygen atom,

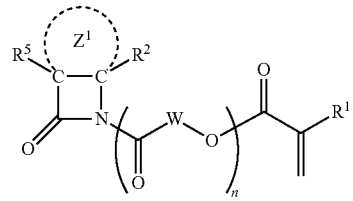

(1-1)

wherein:

R$^1$ represents a hydrogen atom, a methyl group, or a trifluoromethyl group;

each of R$^2$ and R$^5$ independently represents a hydrogen atom or an alkyl group having a carbon number of from 1 to 5;

W represents an alkylene group having a carbon number of from 1 to 10 or a cycloalkylene group having a carbon number of from 4 to 10;

n represents 0 or 1; and

Z$^1$ represents a ring formed together with the two carbon atoms on the β-lactam, with a number of atoms forming the ring being from 3 to 10.

6. A photoresist composition, comprising the polymer of claim 5, a photo acid generator, and a solvent.

7. A method for producing a polymer, comprising a step of polymerizing an N-acyl-β-lactam derivative represented by formula (1):

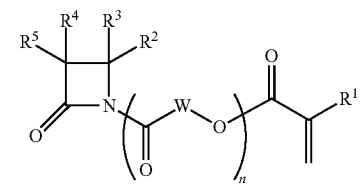

(1)

wherein:

R$^1$ represents a hydrogen atom, a methyl group, or a trifluoromethyl group;

W represents an alkylene group having a carbon number of from 1 to 10 or a cycloalkylene group having a carbon number of from 4 to 10;

n represents 0 or 1; and each of R$^2$, R$^3$, R$^4$, and R$^5$ independently represents a hydrogen atom, an alkyl group having a carbon number of from 1 to 5, a cyclic hydrocarbon group having a carbon number of from 3 to 10, or an acyloxy group having a carbon number of from 2 to 6, provided that R$^3$ and R$^4$ are connected to each other to form a substituted or unsubstituted ring 2) having a ring forming atom number of from 4 to 10, said ring 2) optionally comprising an oxygen atom.

8. A method for producing a polymer, comprising the step of polymerizing an N-acyl-β-lactam derivative represented by formula (1-1):

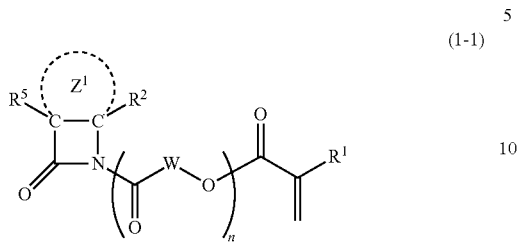

(1-1)

wherein:
- $R^1$ represents a hydrogen atom, a methyl group, or a trifluoromethyl group;
- each of $R^2$ and $R^5$ independently represents a hydrogen atom or an alkyl group having a carbon number of from 1 to 5;
- W represents an alkylene group having a carbon number of from 1 to 10 or a cycloalkylene group having a carbon number of from 4 to 10;
- n represents 0 or 1; and
- $Z^1$ represents a ring formed together with the two carbon atoms on the β-lactam, with a number of atoms forming the ring being from 3 to 10.

9. The method of claim 7 or 8, wherein n is 1.

10. The method of claim 7 or 8, wherein n is 0.

* * * * *